(12) United States Patent
Hwang et al.

(10) Patent No.: US 8,355,140 B2
(45) Date of Patent: Jan. 15, 2013

(54) SYSTEMS CONFIGURED TO GENERATE OUTPUT CORRESPONDING TO DEFECTS ON A SPECIMEN

(75) Inventors: Shiow-Hwei Hwang, Livermore, CA (US); Tao-Yi Fu, Fremont, CA (US); Xiumei Liu, Santa Clara, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 13/080,647

(22) Filed: Apr. 5, 2011

(65) Prior Publication Data

US 2011/0181891 A1    Jul. 28, 2011

Related U.S. Application Data

(62) Division of application No. 11/461,893, filed on Aug. 2, 2006, now Pat. No. 7,924,434.

(60) Provisional application No. 60/704,738, filed on Aug. 2, 2005.

(51) Int. Cl.
*G01B 9/02* (2006.01)
(52) U.S. Cl. .......................... 356/511; 356/520
(58) Field of Classification Search .................. 356/520
See application file for complete search history.

(56) References Cited

U.S. PATENT DOCUMENTS

| | | | |
|---|---|---|---|
| 3,697,184 A * | 10/1972 | Lehmbeck | 356/404 |
| 3,706,492 A | 12/1972 | Roblin et al. | |
| 4,465,366 A | 8/1984 | Schmidt | |
| 5,192,982 A | 3/1993 | Lapucci | |
| 5,524,152 A | 6/1996 | Bishop et al. | |
| 5,710,631 A * | 1/1998 | Bou-Ghannam et al. | 356/495 |
| 5,825,492 A | 10/1998 | Mason | |
| 5,883,714 A | 3/1999 | Jann et al. | |
| 6,233,056 B1 | 5/2001 | Naulleau et al. | |
| 6,587,194 B2 * | 7/2003 | Karpol et al. | 356/237.5 |
| 6,597,446 B2 | 7/2003 | Klooster et al. | |
| 2003/0085335 A1 | 5/2003 | Almogy et al. | |
| 2003/0147083 A1 | 8/2003 | Hill | |

(Continued)

FOREIGN PATENT DOCUMENTS

EP        0526734        2/1993

(Continued)

OTHER PUBLICATIONS

International Search Report and Written Opinion for PCT/US06/30296 mailed Mar. 29, 2007.

(Continued)

*Primary Examiner* — Tarifur Chowdhury
*Assistant Examiner* — Jonathon Cook
(74) *Attorney, Agent, or Firm* — Ann Marie Mewherter

(57) ABSTRACT

Systems configured to generate output corresponding to defects on a specimen and systems configured to generate phase information about defects on a specimen are provided. One system includes an optical subsystem that is configured to create interference between a test beam and a reference beam. The test beam and the reference beam are reflected from the specimen. The system also includes a detector that is configured to generate output representative of the interference between the test and reference beams. The interference increases contrast between the output corresponding to the defects and output corresponding to non-defective portions of the specimen.

12 Claims, 11 Drawing Sheets

U.S. PATENT DOCUMENTS

2004/0130710 A1  7/2004  Hwang et al.
2004/0257587 A1* 12/2004  Rosakis et al. ................ 356/520
2005/0030545 A1*  2/2005  Tuschel et al. ................ 356/454

FOREIGN PATENT DOCUMENTS

WO  2004/025379  3/2004
WO  2004/025567  3/2004
WO  2004/025568  3/2004
WO  2004/111623  12/2004

OTHER PUBLICATIONS

International Preliminary Report on Patentability for PCT/US06/30296 mailed Feb. 14, 2008.
M. Takeda, "Spatial carrier heterodyne techniques for precision interferometry and profilometry: An overview.", Proc. SPIE vol. 1121, pp. 73-88, 1989.

* cited by examiner

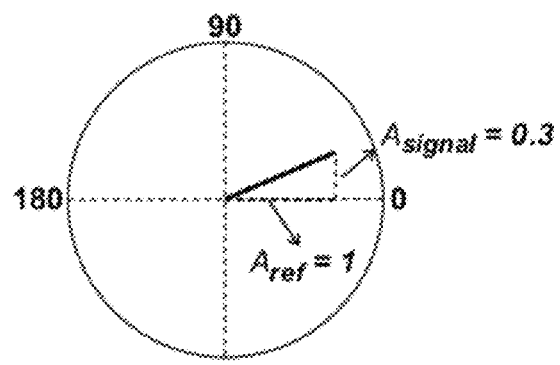 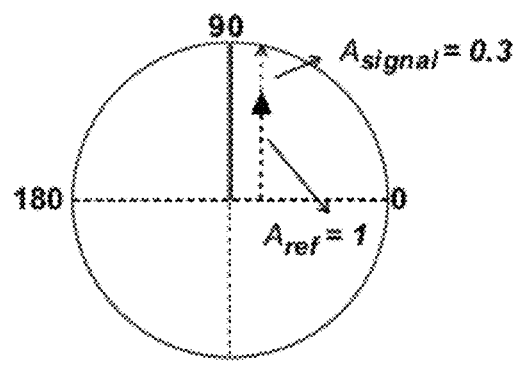
FIG. 3    FIG. 4
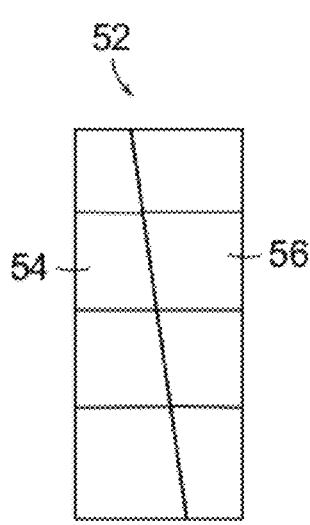 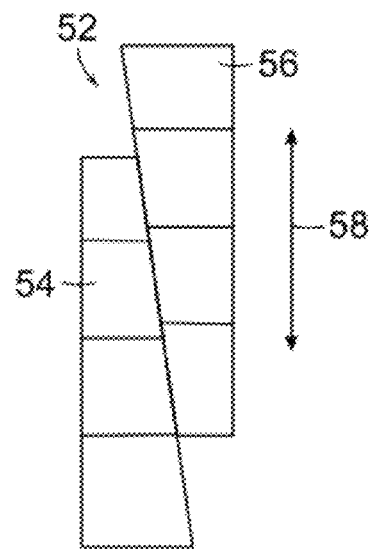
FIG. 6    FIG. 7

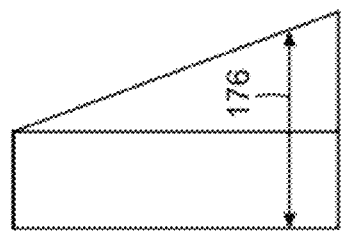
FIG. 19
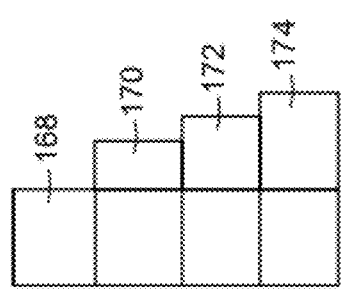
FIG. 18
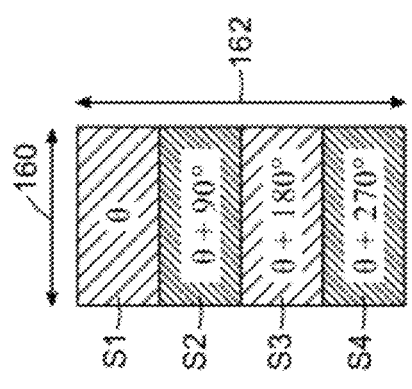
FIG. 17
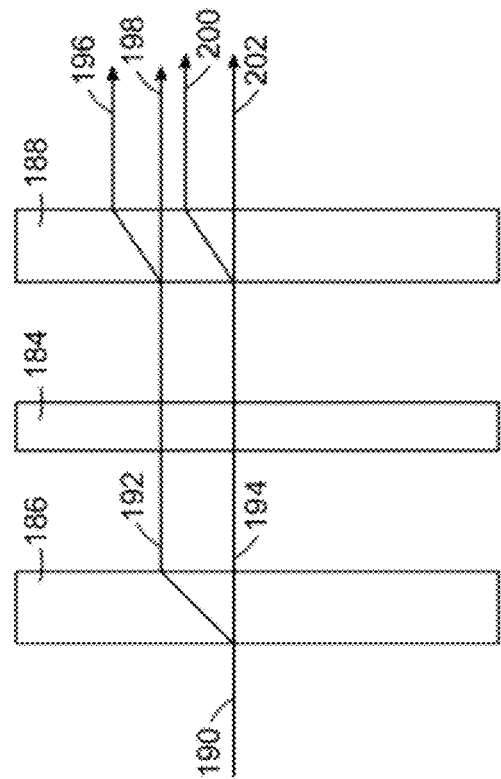
FIG. 21
FIG. 20

SYSTEMS CONFIGURED TO GENERATE OUTPUT CORRESPONDING TO DEFECTS ON A SPECIMEN

CROSS-REFERENCE TO RELATED APPLICATIONS

This application is a divisional of U.S. patent application Ser. No. 11/461,893 filed Aug. 2, 2006, issued as U.S. Pat. No. 7,924,434 on Apr. 12, 2011, which claims priority to U.S. Provisional Application No. 60/704,738 entitled "Systems Configured to Generate Signals Corresponding to Defects on a Wafer," filed Aug. 2, 2005, which is incorporated by reference as if fully set forth herein.

BACKGROUND OF THE INVENTION

1. Field of the Invention

This invention generally relates to systems configured to generate output corresponding to defects on a specimen. Certain embodiments relate to systems that include an optical subsystem that is configured to create interference between a test beam and a reference beam, both of which are reflected from a specimen.

2. Description of the Related Art

The following description and examples are not admitted to be prior art by virtue of their inclusion in this section.

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various times during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Many different types of inspection tools have been developed for the inspection of semiconductor wafers. Defect inspection is currently being performed using techniques such as bright field (BF) imaging, dark field (DF) imaging, and scattering. Phase detection is typically performed using spatial fringe modulation. The type of inspection tool that is used for inspecting semiconductor wafers may be selected based on, for example, characteristics of the defects of interest and characteristics of the wafers that will be inspected.

There are, however, many disadvantages to currently used inspection systems. For instance, as design rules shrink, the amplitude perturbations and complex fields resulting from defects are significantly weaker compared to those resulting from the object being inspected. With BF mode, because of the small amplitude perturbations, the contrast of the defect image is relatively low making the defect extremely difficult to detect. For DF mode, the defect contrast is generally satisfactory; however, the raw signal is typically so weak that the signal is not above the sensor noise. The raw signal may be increased by increasing the intensity of the illumination used for the DF mode. However, to increase the DF signal to useful levels, the required increase in the illumination level is impractical due to source availability or wafer damage risk.

Currently, defect inspection based on phase detection using the spatial fringe technique is susceptible to system noise, has higher costs for image processing, and is limited by the sampling of the fringe. For example, systems and methods that can be used for defect inspection based on phase information are illustrated in International Publication Nos. WO 2004/025379 by Thomas et al, WO 2004/025567 by Dal et al., and WO 2004/025568 by Voelki, which are incorporated by reference as if fully set forth herein. As described in these publications, a reference image is compared to an image of a target to detect defects on the target. The reference image can be an image reflected from a reference beam mirror or an image generated from a different position on the target than the target image. Therefore, these systems and methods will be particularly susceptible to noise such as that caused by system vibration and variations in focus at the different positions on the target. In addition, as described in these publications, relatively complex image processing techniques are used to reduce the non-defective aberrations between the images being compared. The image processing techniques not only increase cost and reduce throughput, but more importantly may undesirably alter the image data such that defects, and particularly defects of relatively small size, are detected with less accuracy.

Accordingly, it may be advantageous to develop a system that is configured to generate output corresponding to defects on a specimen by increasing the contrast between the output corresponding to the defects and output corresponding to non-defective portions of the specimen using an interference contrast enhancement technique thereby increasing the accuracy of the system for detecting defects, and particularly relatively small defects, while reducing the susceptibility of the system to noise, eliminating the need for time consuming and expensive image processing, and providing flexibility in the system for detecting multiple types of defects.

SUMMARY OF THE INVENTION

The following description of various system embodiments is not to be construed in any way as limiting the subject matter of the appended claims.

One embodiment relates to a system configured to generate output corresponding to defects on a specimen. The system includes an optical subsystem configured to create interference between a test beam and a reference beam. The test beam and the reference beam are reflected from the specimen. The system also includes a detector configured to generate output representative of the interference between the test and reference beams. The interference increases contrast between the output corresponding to the defects and output corresponding to non-defective portions of the specimen. In this manner, the above-described system can be used for inspection and/or defect review of the specimen based on interference contrast using a "self-generated" reference beam.

The above-described system may also, therefore, be used for interference contrast enhancement. In some such embodiments, the system may be configured for "axial" differential interference contrast (DIC), in which the reference beam is used as a "low resolution copy" of the test beam. For example, in one embodiment, the reference beam and the test beam are reflected from the same measurement spot on the specimen. In one such embodiment, the reference beam has a lower resolution than the test beam. In another embodiment, the reference beam and the test beam have different imaging pupil profiles. In a preferred embodiment, the reference beam is oriented such that the phase of the reference beam is substantially parallel to the phase of a portion of the test beam reflected from the defects. For example, in some embodiments, the system is configured to adjust the reference beam such that the reference beam can be oriented to be in-phase with a portion of the test beam reflected from the defects to increase the contrast.

In some embodiments in which the system can be used for axial DIC, the optical subsystem includes a group of two wedge prisms. In one such embodiment, the system is configured to move a first of the two wedge prisms with respect to a second of the two wedge prisms to alter relative phase between the reference and test beams. In different embodiments, the optical subsystem includes a mirror. In such embodiments, the system is configured to alter a position of the mirror to alter relative phase between the reference and test beams. In additional embodiments, the optical subsystem includes one or more optical components configured to alter the relative amplitude ratio and phase between the reference and test beams.

In another embodiment in which the system can be used for axial DIC, the optical subsystem is configured to direct the test and reference beams coli In early along an optical path. In one such embodiment, the test and reference beams have different polarizations.

In embodiments different than those described above, the system may be used for interference contrast enhancement, but the reference beam and the test beam may be laterally spaced from each other in the optical path of the optical subsystem. In this manner, the system may be configured for "lateral" DIC. In some such embodiments, the reference beam and the test beam have substantially the same resolution, but portions of the test and reference beams that interfere with each other are reflected from neighboring, substantially identical structures on the specimen. For example, in one embodiment, the optical subsystem is configured to laterally shift the reference beam with respect to the test beam. In another embodiment, the optical subsystem is configured such that portions of the reference beam and the test beam that interfere with each other are reflected from substantially identical patterns spaced from each other on the specimen. The reference beam and the test beam may have polarizations that are orthogonal to each other.

In an additional embodiment in which the system can be used for lateral DIC, the optical subsystem includes a wedge element that includes a concave element and a convex element. In such an embodiment, the system is configured to move one or more of the concave and convex elements with respect to each other to create lateral shift between the test beam and the reference beam. In one such embodiment, the wedge element is formed of a birefringent material. In a further embodiment, the optical subsystem is configured such that the test and reference beams are imaged with different pupil apertures. For example, the test beam can be imaged in bright field (BF) mode, and the reference beam can be imaged in dark field (DF) mode. In another example, the test beam can be imaged in DF mode, and the reference beam can be imaged in BF mode.

In some embodiments in which the system can be used for lateral DIC, the optical subsystem is configured to alter the relative amplitude and phase between the reference beam and the test beam substantially continuously. In additional embodiments, the defects for which the interference increases the contrast of the output corresponding to the defects include different types of defects.

As described above, the system may be configured for axial DIC or lateral DIC. However, the system may also be configured to perform both axial DIC and lateral DIC. Axial DIC and lateral DIC may be performed substantially simultaneously or sequentially. For example, in another embodiment, the optical subsystem is configured to create interference between the test beam and an additional reference beam. The reference beam has a lower resolution than the test beam, and the additional reference beam and the test beam are laterally shifted from each other.

The system embodiments described above may also be configured for interference contrast (e.g., axial DIC and/or lateral DIC) and another mode of inspection. For example, in another embodiment, the optical subsystem is configured to generate an additional test beam reflected from the specimen. In such an embodiment, the system may include an additional detector that is configured to generate BF output representative of the additional test beam. In one such embodiment, the output and the BF output are generated simultaneously. In a further embodiment, the optical subsystem is configured to collect an additional test beam scattered from the specimen. In such an embodiment, the system also includes an additional detector that is configured to generate DF output representative of the additional test beam. The output and the DF output may be generated substantially simultaneously.

In any of the above-described embodiments of the system configured for axial DIC, lateral DIC, another inspection mode, or some combination thereof, the system may be configured for inspection of the specimen. The specimen may be a wafer or a reticle. In other embodiments, the system is configured for review of the defects on the specimen. The specimen may be a wafer or reticle. Each of the embodiments of the system configured for interference contrast described above may be further configured as described herein.

In embodiments different than all of those described above, a system that may be used for inspection and/or defect review of a specimen based on interference contrast using a self-generated reference beam is configured for relative phase measurement using spatial fringe techniques, instead of interference contrast enhancement as described above. For example, an additional embodiment relates to a system that is configured to generate phase information about defects on a specimen. The system includes an optical subsystem configured to combine a test beam and a reference beam to create an interference beam. The test beam and the reference beam are reflected from the specimen. The reference beam has a lower resolution than the test beam and is laterally shifted from the test beam in the pupil space of the optical subsystem to create spatial fringes at an image plane of the optical subsystem. The system also includes a detector configured to generate output representative of the spatial fringes at the image plane. The output can be used to determine the phase information about the defects. The system described above may be further configured as described herein.

In embodiments different than all of those described above, a system that may be used for inspection and/or defect review of a specimen based on interference contrast using a self-generated reference beam is configured for relative phase measurement using phase-shifting techniques. For example, another embodiment relates to a system that is configured to generate phase information about defects on a specimen. This system includes an optical subsystem configured to combine a test beam and a reference beam to create an interference beam. The test beam and the reference beam are reflected from the specimen. The optical subsystem is also configured to alter phase of the reference beam to create different interference beams.

The system also includes a detector that is configured to generate output representative of the different interference beams. The output can be used to determine the phase information about the defects. The optical subsystem is also configured to scan the different interference beams over different segments of the detector. The different segments extend across a portion of one dimension of the detector.

In one embodiment of the above-described system configured for relative phase measurement using phase-shifting techniques, the one dimension of the detector includes a width of the detector. In a different embodiment, the optical subsystem is configured to alter the phase of the reference beam to create the different interference beams for different swaths on the specimen, and the one dimension of the detector includes a height of the detector. In any of these embodiments, the detector may include a time delay integration detector. Alternatively, the detector may include a charge coupled device detector.

In another embodiment of the system configured for relative phase measurement using phase-shifting techniques, the optical subsystem is configured to scan the different interference beams over the different segments of the detector sequentially. In an alternative embodiment, the optical subsystem is configured to scan the different interference beams over the different segments of the detector substantially simultaneously. In one such embodiment, the optical subsystem includes a staged phase wedge. Different stages of the staged phase wedge are configured to alter the phase of the reference beam to different degrees substantially simultaneously.

In a different such embodiment, the optical subsystem includes an optical component that is configured to separate the reference beam into multiple reference beams, and the optical subsystem is configured to alter the phase of the multiple reference beams such that each of the multiple reference beams has a different phase. The optical subsystem is also configured to combine the test beam and the multiple reference beams to create the different interference beams. In one such embodiment, the optical component includes a grating. In a different embodiment, the optical component includes a polarizing component disposed between two birefringent plates. In yet another embodiment, the optical component includes a polarizing component disposed between a grating and a birefringent plate. Each of the embodiments of the system configured for relative phase measurement using phase-shifting techniques described above may be further configured as described herein.

BRIEF DESCRIPTION OF THE DRAWINGS

Other objects and advantages of the invention will become apparent upon reading the following detailed description and upon reference to the accompanying drawings in which:

FIGS. 3-4 are schematic diagrams illustrating examples of different defect signals and how a reference beam having different phases affects the different defect signals;

FIGS. 6-7 are schematic diagrams of a side view of an embodiment of a group of two wedge prisms having different positions with respect to each other;

FIGS. 15-17 are schematic diagrams illustrating various embodiments of different segments of a detector and how different interference beams may be scanned over the different segments by an optical subsystem described herein;

FIGS. 18-19 are schematic diagrams of a side view of different embodiments of a staged phase wedge that may be included in an optical subsystem described herein; and FIGS. 20-21 are partial schematic diagrams of a side view of different embodiments of an optical component that is configured to separate a reference beam into multiple reference beams.

Figure 1:
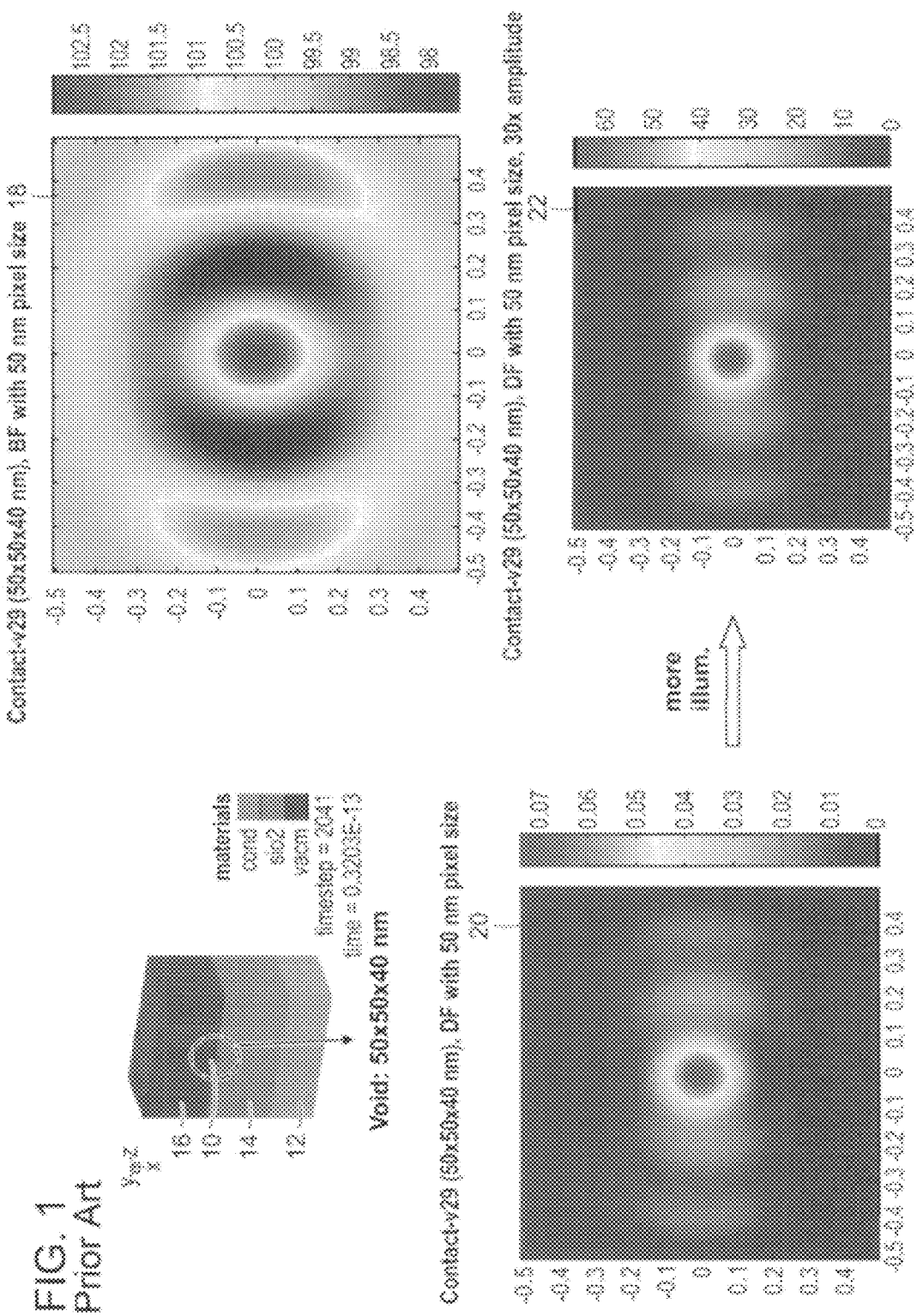
FIG. 1 includes defect images obtained using various types of imaging methods.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on die contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defect" generally refers to any abnormality that may be formed on or within any specimen described herein.

As used herein, the term "specimen" generally refers to a wafer or a reticle (or "mask"). As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may farther include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

As used herein, the term "reticle" or "mask" is generally defined as a transparent substrate such as glass, borosilicate glass, and fused silica having opaque structures formed thereon. The opaque structures may be replaced by regions etched into the transparent substrate. Many different types of reticles are known in the art, and the term reticle as used herein is intended to encompass all types of reticles.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

In general, the systems described herein are configured to perform defect inspection and/or review using interference contrast with a "self-generated" reference beam. Some of the systems are configured to perform an interference contrast enhancement technique. In particular, the systems described herein, unlike systems currently used for defect detection, may use a cross term to increase, and even optimize, the raw signal level and defect contrast. As described further herein, embodiments of the system configured to perform an interference contrast enhancement technique may be configured for "axial" differential interference contrast (DIC) using a self-generated reference beam or "lateral" DIC using a self-generated reference beam. As also described further herein, instead of being configured to perform an interference contrast enhancement technique, embodiments of the system may be configured to perform a relative phase measurement using either spatial fringe techniques or phase shifting techniques.

To illustrate the deficiencies in currently used inspection systems, FIG. 1 illustrates images generated using other types of defect inspection systems. In particular, FIG. 1 illustrates images generated by bright field (BF) and dark field (DF) systems for void defect 10 located in a stack of materials that includes conductor 12, silicon dioxide ($SiO_2$) 14 formed on top of the conductor, and air 16 on top of the $SiO_2$. Void defect 10 has approximate dimensions of 50 nm×50 nm×40 nm.

The images shown in FIG. 1 illustrate that the BF and DF imaging techniques are inadequate for detecting the relatively small void defect. In particular, BF image 18 was obtained for the void defect using a numerical aperture (NA) of 0.9 and a pixel size of 50 nm. As shown in FIG. 1, BF image 18 has sufficient raw signal, but the contrast is not sufficient for defect detection. In particular, the contrast of the BF image is about 2.6%. DF image 20 was obtained for the same void defect. The contrast of the DF image was about 100%, but the raw signal is insufficient for defect detection. To increase the raw signal, the same DF imaging technique was performed for the defect but with an illumination intensity that was 900 times higher than that used to generate DF image 20, DF image 22 was obtained with the higher intensity illumination and a pixel size of 50 nm. This DF image has relatively good contrast, but still not enough signal for defect detection. In addition, using such high intensity illumination may be impractical for most defect inspection and/or review systems.

In general, the systems described herein are configured to enhance defect signals such as those illustrated in FIG. 1 through interference contrast using a "self-generated" beam as a reference. This self-generated reference beam may be generated by splitting part of the signal or test beam reflected from the specimen. In this manner, the reference beam is created or "self-generated" from the test beam. The self-referencing beam may then be recombined with the test beam as described herein to create interference contrast. In this manner, the system embodiments described herein may be used for inspection and/or defect review based on interference contrast using a self-generated reference beam. In particular, the system is configured for inspection of a specimen according to one embodiment, and the specimen may be a wafer or a reticle. In another embodiment, the system is configured for review of defects on a specimen, and the specimen may be a wafer or a reticle.

As described above, the systems embodiments may be configured for interference contrast enhancement. In one such embodiment, a system configured to generate output corresponding to defects on a specimen includes an optical subsystem configured to create interference between a test beam and a reference beam. The test beam and the reference beam are reflected from the specimen. The system also includes a detector configured to generate output representative of the interference between the test and reference beams. The interference increases contrast between the output corresponding to the defects and output corresponding to non-defective portions of the specimen. Such a system may be further configured as described and illustrated herein.

Figure 2:
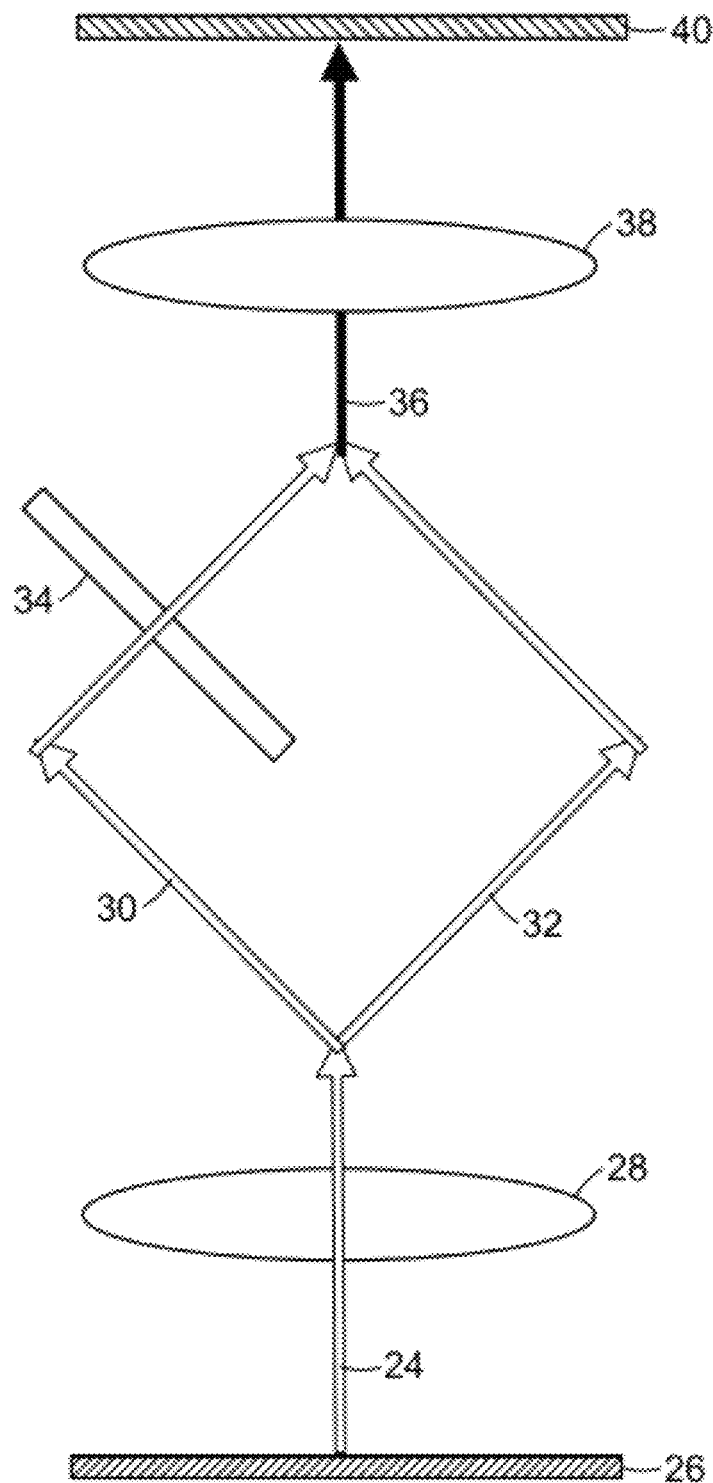
FIG. 2 is a partial schematic diagram of a side view of an embodiment of a system that is configured to generate output corresponding to defects on a specimen.

In one embodiment of a system configured for interference contrast enhancement, the system is configured for "axial" DIC in which the reference beam is a "low resolution copy" of the test beam. For example, FIG. 2 illustrates one embodiment of a system that is configured to generate output corresponding to defects (not shown) on a specimen. This system is configured for axial DIC, in which the self-generated reference beam is used as a low resolution copy of the test beam. In particular, as shown in FIG. 2, light 24 reflected from specimen 26 is collected by lens 28. Although lens 28 is shown in FIG. 2 to be a refractive optical component, it is to be understood that a reflective collector may be used in place of refractive lens 28. In another alternative, lens 28 may be replaced by a combination of refractive and reflective components. In addition, although lens 28 is shown as a single lens, it is to be understood that lens 28 may be a compound lens or may be replaced by multiple lenses.

Light collected by lens 28 is split into reference beam 30 and test beam 32. Therefore, both the reference beam and the test beam have been reflected from the specimen. In one embodiment, the reference beam and the test beam are reflected from the same measurement spot (not shown) on the specimen (i.e., as light 24 before it is split into the reference and test beams). In one such embodiment, the reference beam has a lower resolution than the test beam. The light may be split into the reference and test beams using any appropriate optical component known in the art such as a beam splitter (not shown in FIG. 2). As shown in FIG. 2, the test and reference beams travel along split paths (i.e., non-coaxial paths).

The system shown in FIG. 2 includes an optical subsystem that is configured to create interference between test beam 32 and reference beam 30. For instance, one or more optical components (not shown in FIG. 2) such as those described further herein may be disposed along the path of the reference and/or test beams. In one embodiment, the optical subsystem includes an optical component (not shown in FIG. 2) that is configured to alter the relative phase between the reference beam and the test beam. Therefore, recombination of the test and reference beams will cause interference between the reference and test beams. In some embodiments, the optical subsystem includes optical component 34, which is configured to alter the relative amplitude ratio of reference beam 30 and test beam 32. In addition, the optical subsystem may include more than one such amplitude-altering optical components. The amplitude-altering component(s) may include, for example, one or more filters, one or more polarizing components, etc. The amplitude of the reference beam may be altered depending on, for example, the amplitude of the non-defective portions of the test beam as described further herein.

The test and reference beams may be recombined using any suitable optical component known in the art such as an appropriately positioned beam splitter (not shown in FIG. 2). Recombined beam 36 may be focused by lens 38 onto detector 40 of the system. Lens 38 may be configured as described above with respect to lens 28. Detector 40 is configured to generate output representative of the interference between the test and reference beams. The interference preferably increases contrast between the output corresponding to the defects and output corresponding to non-defective portions (not shown) of the specimen. Detector 40 may include any appropriate detector known in the art, such as a charge coupled device (CCD) or a time delay integration (TDI) detector. The optical subsystem may be configured to scan the recombined beam or "interference beam" over the detector as described further herein.

The system shown in FIG. 2 may include a number of additional components that are not shown in FIG. 2. For example, the optical subsystem may include a light source for illuminating the measurement spot on the specimen. The light source may be coupled to one or more optical components that are configured to direct the light onto the specimen at an appropriate angle of incidence (e.g., normal incidence). The light source may be any appropriate light source known in the art. In addition, the light source may be configured to generate light having any appropriate characteristics (e.g., wavelength, intensity, polarization, coherence, etc.) known in the art.

The system may also include a processor or computer system. The processor or computer system may be configured to detect defects on the specimen using the output generated by detector 40. In this manner, the system shown in FIG. 2 may be configured for inspection of the specimen. The processor or computer system may also or alternatively be configured to perform review of the defects on the specimen using the output generated by detector 40. In this manner, the system shown in FIG. 2 may be configured for review of the defects on the specimen. In addition, the processor or computer system may be configured to perform any other defect-related function(s) known in the art. The processor or computer system may include any appropriate processor or computer system known in the art. The system shown in FIG. 2 may be further configured as described herein.

One way to maximize the benefits of the systems described herein is to adjust the reference beam so that the phase of the reference beam is substantially parallel to the phase of the defect signal and has an intensity that enhances the defect contrast and balances the overall signal range. For example, the phase of the reference beam may be oriented at about 0 degrees with respect to the phase of the defect signal to produce constructive interference between the reference beam and the defect signal. Alternatively, the phase of the reference beam may be oriented at about 180 degrees with respect to the phase of the defect signal to produce destructive interference between the reference beam and the defect signal. FIG. 3 illustrates one example of a reference signal that is not in-phase with a defect signal. The reference signal has an amplitude, $A_{ref}$, of 1, and the amplitude of the defect signal, $A_{signal}$, is 0.3. When these reference and defect signals are combined as described above, the resulting intensity measured by the detector or sensor may be determined according to the following equation:

$$I_{CCD} = |A_{signal} e^{i\Phi_{signal}} + A_{ref} e^{i\Phi_{ref}}|^2 = A_{signal}^2 + A_{ref}^2 + 2A_{signal}A_{ref}\cos(\Phi_{signal} - \Phi_{ref})$$

Therefore, for these out-of-phase signals, the intensity detected by the detector, $I_{sensor}$, will be equal to $1^2 + 0.3^2 = 1.09$.

In contrast, FIG. 4 illustrates one example of a reference signal that is in-phase with a defect signal. In this example, the amplitudes of the defect signal and the reference signal are the same as those described above (e.g., $A_{ref}=1$, $A_{signal}=0.3$). However, in this case, $I_{sensor}$ is $(1+0.3)^2=1.69$. Therefore, the intensity detected for interference between a reference beam that is in-phase with a portion of the test beam reflected from a defect is higher than that for interference caused by a reference beam that is out-of-phase with the defect portion of the test beam.

Accordingly, to translate "defect perturbation" into an observable intensity difference on the detector through interference contrast enhancement, the orientation of the phase of the reference signal is preferably substantially parallel to the phase of the defect perturbation to maximize the detectable signal. In one embodiment, the reference beam is oriented such that the phase of the reference beam is substantially parallel to the phase of a portion of the test beam reflected from the defects. In addition, for defects having substantially small amplitude perturbations, it is particularly desirable to have the capability to adjust the relative phase and amplitude of the reference beam. For example, in some embodiments, the system is configured to adjust the reference beam such that the reference beam can be oriented to be in-phase with a portion of the test beam reflected from the defects to increase the contrast. The system may be configured to adjust the reference beam in this manner according to any of the embodiments described herein. In this manner, the defect contrast can be optimized for any kind of defect and any kind of specimen structures.

Figure 5:
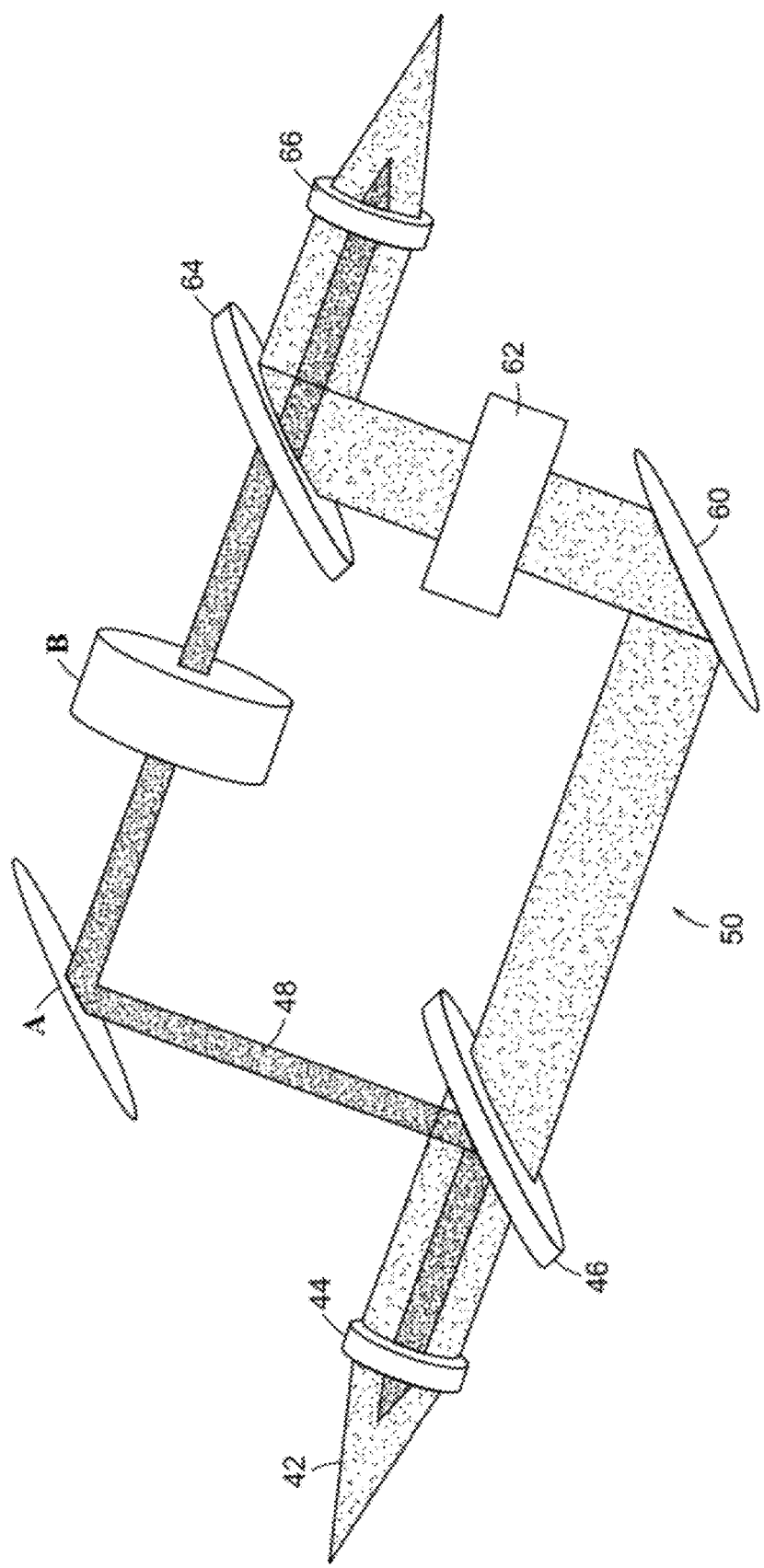
FIG. 5 is a partial schematic diagram of a side view of one embodiment of an optical subsystem that may be included in a system that is configured to generate output corresponding to defects on a specimen.

FIG. 5 illustrates one embodiment of an optical subsystem that may be included in a system that is configured to generate output corresponding to defects on a specimen. This embodiment of the optical subsystem may be included in a system configured for interference contrast enhancement using axial DIC in which the reference beam is a low resolution copy of the test beam. As shown in FIG. 5, light 42 reflected from a specimen (not shown in FIG. 5) is collected by lens 44. Lens 44 may be configured as described above. For example, lens 44 may be an objective lens. Light collected by lens 44 is split by optical component 46 into reference beam 48 and test beam 50. In this manner, the reference beam is self-generated from the test beam reflected from the specimen. Optical component 46 may include any suitable optical component known in the art such as a beam splitter. As shown in FIG. 5, therefore, the test and reference beams travel along split paths (i.e., non-coaxial paths).

In some embodiments, the optical subsystem includes mirror A and optical component B. Reference beam 48 is directed by mirror A to optical component B. Mirror A may be a simple folding mirror. However, in one embodiment, the system is configured to alter a position of the mirror to alter relative phase between the reference and test beams. The system may include any suitable mechanical component(s) (not shown) that can be coupled to mirror A and that can be controlled (e.g., by a processor (not shown) such as that described above) to alter a position of the mirror. In a different embodiment, optical component B includes a group of two wedge prisms (not shown in FIG. 5). In one embodiment, therefore, the optical subsystem includes a group of two wedge prisms. In one such embodiment, the system is configured to move a first of the two wedge prisms with respect to a second of the two wedge prisms to alter relative phase between the reference and test beams.

FIG. 6 illustrates one embodiment of group 52 that includes wedge prisms 54 and 56. Wedge prisms 54 and 56 may be formed of any suitable material known in the art and may have any suitable configuration known in the art. As shown in FIG. 7, the system may be configured to move or slide wedge prism 54, wedge prism 56, or both of the wedge prisms in the direction indicated by arrow 58. In one such embodiment, the system may include any suitable mechanical component(s) (not shown) that can be coupled to one or both of the wedge prisms and that can be controlled as described above to alter a position of one or both of the wedge prisms. By controlling the relative phase of the reference beam by moving one or both of wedge prisms 54 and 56, the optical path difference of the reference beam may be altered on the order of waves. Preferably, mirror A or optical component B is configured to orient the reference beam to be in-phase with a portion of the test beam reflected from the defects to maximize the interference contrast enhancement of the defect signal as described above.

In some embodiments, the system may be configured to alter a position of the phase-altering component (e.g., mirror A or wedge prisms of optical component B) substantially continuously thereby altering the phase of the reference beam substantially continuously. In an additional embodiment, the optical subsystem shown in FIG. 5 includes one or more optical components (such as optical component 34 shown in FIG. 2) that are configured to alter the relative amplitude ratio between the reference and test beams. In some embodiments, the one or more amplitude-altering optical components may be configured to alter the relative amplitude ratio between the reference and test beams substantially continuously. For example, the amplitude-altering optical component(s) may include one or more polarizing components that can be controlled to alter the relative amplitude ratio between the reference and test beams substantially continuously. The amplitude-altering component(s) may be controlled by the system or the subsystem in any manner known in the art. In this manner, the optical subsystem may be configured to alter the relative amplitude and phase between the reference and test beams substantially continuously.

As described above, interference contrast enhancement of the defect signal is maximized when the reference beam and the test beam are in-phase. Therefore, continuously adjusting the relative phase between the reference and test beams increases the likelihood that the reference beam and the test beam are in-phase at some point during the measurement. As such, the system may preferably be configured to have continuous adjustability of the relative amplitude and phase between the reference and test beams for defect signal optimization. Such continuous adjustment of the relative amplitude and phase between the reference and test beams may be particularly advantageous when different types of defects are present on the specimen, each of which may alter the phase of the illumination to a different degree. Therefore, the systems described herein may be configured such that the relative phase and amplitude between the reference and test beams can be adjusted to optimize the signal of any defect of interest (DOI). In one embodiment, therefore, die defects for which the interference increases the contrast include different types of defects. In this manner, the defect output that can be enhanced by interference contrast as described herein may include different types of defects, and the system can be configured to detect and/or review different types of defects using defect output having the best possible contrast and amplitude.

Referring back to FIG. 5, the optical subsystem may be configured such that the reference beam and the test beam have substantially equivalent reduced optical lengths. For example, test beam 50 is reflected by mirror 60, which directs the test beam to optical component 62. Optical component 62 may include a group of two wedge elements (not shown in FIG. 5) that is substantially equivalent to that of optical component B. However, unlike mirror A and optical component B, mirror 60 and optical component 62 may not be configured to alter the phase of the test beam. For instance, the position of mirror 60 may be static or substantially constant. In addition, the positions of the wedge elements of optical component 62 may also be static. In this manner, aberrations in the recombined beams due to differences in the optical path can be eliminated.

As shown in FIG. 5, the optical subsystem includes optical component 64, which is configured to recombine the reference beam and the test beam thereby creating interference between the test beam and the reference beam. In one embodiment, optical component 64 is an appropriately positioned 45° beam splitter. The recombined beam or "interference beam" is directed through lens 66. Lens 66 may be configured as described above. Lens 66 is configured to direct the interference beam to a detector (not shown in FIG. 5). The detector is configured to generate output representative of the interference between the test and reference beams. The detector may be further configured as described herein.

The self-referencing beams described herein can be constructed in several ways to improve the defect contrast relative to the nominal pattern with interference contrast enhancement. The specific mechanism selected may vary depending on the patterned structure being inspected. One embodiment of an appropriate reference beam is a low resolution copy of the specimen signal or test beam. A reference beam that is a low resolution copy of the test beam may be substantially similar to a plane wave. In other words, the self-generated reference beam may be an aperture-down copy of the specimen signal or test beam to simulate a plane reference beam.

Such a reference beam can be used in the optical subsystem shown in FIG. 5. In particular, the reference beam and the test beam are reflected from the same measurement spot on the specimen as shown in FIG. 5, and the reference beam may have a lower resolution than the test beam. One advantage of such a reference beam is that interference of the reference beam with the test beam will minimize the DC portion of the test beam thereby allowing better management of the signal dynamic range for increasing the defect contrast. The optical subsystem shown in FIG. 5 may be further configured as described herein. For example, the optical subsystem shown in FIG. 5 may be included in a system configured as an inspection and/or a review system.

In another embodiment, the reference beam is reflected from the same measurement spot in a field on the specimen as the test beam, but the polarization of the reference beam is rotated (with e.g. half-wave plate) so it may have a different polarization than the test beam (e.g., for cross-polarization). In this manner, the system may be configured for inspection and/or review using cross-polarization. Such a reference beam may be particularly suitable for detecting a defect signature that is characteristic of a specific defect such that different types of defects may be distinguished from one another.

In the optical subsystem described above and other embodiments described herein, at least one self-generated reference beam is split from the test beam into a separate path, and the reference and test beams are recombined to generate interference. In different embodiments, the optical subsystem is configured to direct the test and reference beams collinearly or co-axially along an optical path. In some such embodiments, the test and reference beams have different polarizations and are made to interfere using a properly set analyzer. For example, the reference beam and the test beam may have polarizations that are orthogonal to each other. In this manner, the reference beam can propagate in the same optical path as the test beam, and the polarization signal of the reference beam can be used to differentiate it from the test beam. Since two beams with orthogonal polarizations will not interfere with each other, an optical element such as an analyzer (e.g., such as analyzer 90 shown in FIG. 8) may be used to alter the polarization of the reference beam or the test beam such that the reference and test beams have common polarizations prior to being recombined and will interfere with each other upon recombination.

Figure 8:
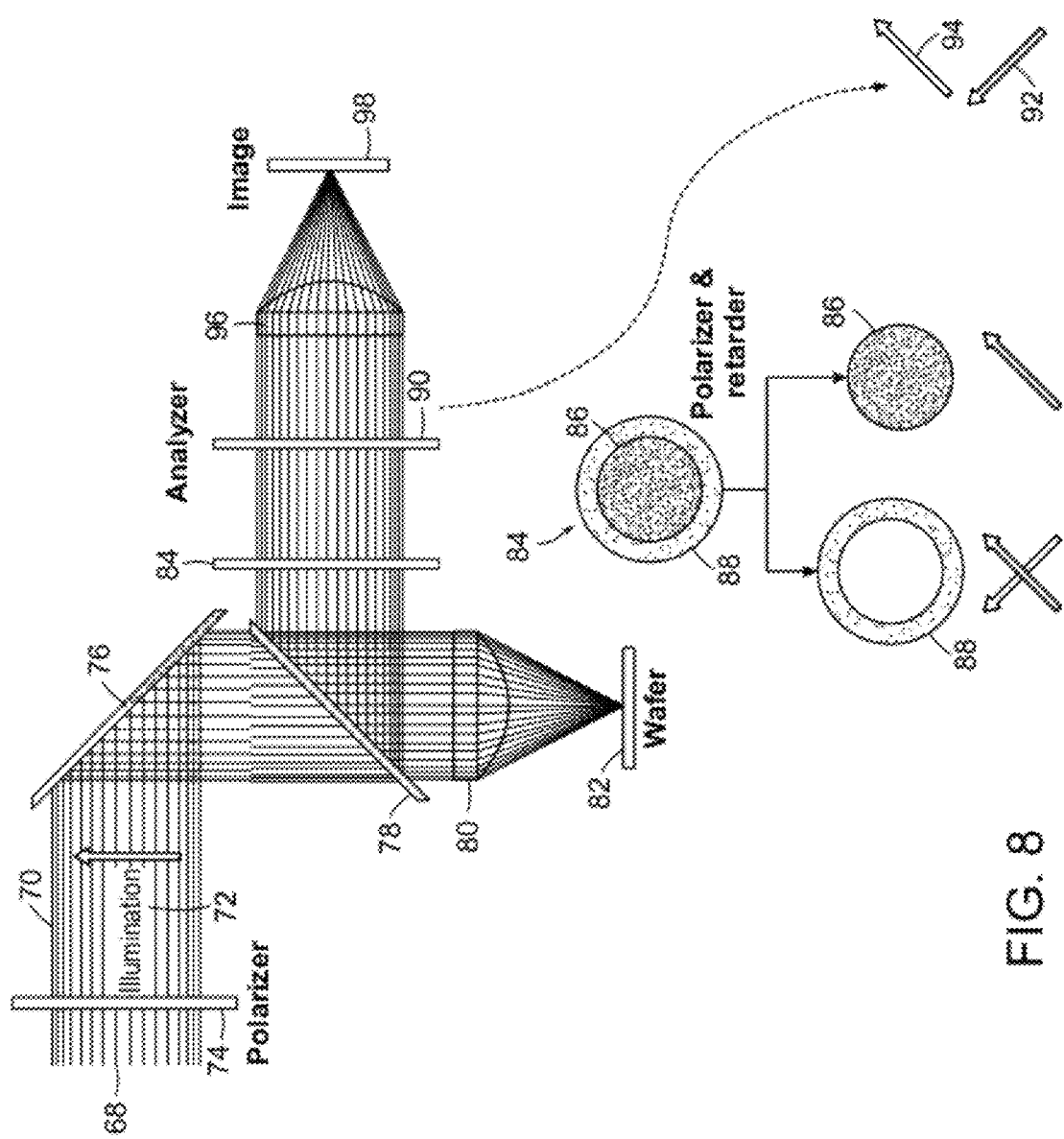
FIGS. 8-9 are partial schematic diagrams of a side view of different embodiments of an optical subsystem that may be included in a system configured to generate output corresponding to defects on a specimen.

FIG. 8 illustrates another embodiment of an optical subsystem that can be included in a system that is configured to generate output corresponding to defects on a specimen. This embodiment of the optical subsystem may be included in a system configured for interference contrast enhancement using axial DIC in which the reference beam is a low resolution copy of the test beam. In this embodiment, the reference and test beams are directed along collinear optical paths. In particular, as shown in FIG. 8, illumination 68 is generated by a light source (not shown), which may be configured as described above. Illumination 68 includes ring illumination 70 or "edge contrast" illumination that is used for the reference beam. The edge contrast illumination may be used for a low resolution reference beam. However, any other suitable type of illumination may be used for the reference beam. Illumination 68 also includes illumination 72 located within the ring illumination. Illumination 72 provides illumination for the test beam.

Illumination 68 is directed through polarizer 74. Polarizer 74 may be configured to alter the polarization of both ring illumination 70 and illumination 72. Alternatively, polarizer 74 may be configured to alter the polarization of ring illumination 70 or illumination 72. Polarizer 74 may include any suitable polarizer known in the art. Light from polarizer 74 is directed by folding mirror 76 through beam splitter 78 and objective lens 80 and onto specimen 82. Folding mirror 76, beam splitter 78, and objective 80 may be configured as described herein and may include any suitable optical components known in the art. Ring illumination 70 used for the reference beam and illumination 70 used for the test beam are directed to the same measurement spot on the specimen.

Light reflected from the specimen is collected by objective lens 80 and is reflected by beam splitter 78 to optical component 84 located at the pupil of the optical subsystem. Therefore, the reference beam and the test beam are reflected from the same measurement spot on the specimen. As described above, the ring illumination provides illumination for the reference beam, and illumination located within the ring illumination provides illumination for the test beam. Therefore, in this embodiment, the reference beam and the test beam have different imaging pupil profiles. As shown in the cross-section of optical component 84, the optical component includes polarizer 86 and retarder 88. Polarizer 86 is configured to alter the polarization of the test beam. One example of the altered test beam polarization is shown below the cross-section of optical component 84. Polarizer 86 may include any suitable polarizer known in the art. Retarder 88 is configured to alter the polarization of the reference beam, and one example of the altered reference beam polarization is also shown below the cross-section of optical component 84. In some embodiments, the retarder may be a variable phase retarder such that the retarder alters the relative phase of the reference beam. One example of a suitable retarder is a birefringent crystal.

After the test and reference beams pass through optical component 84, the beams are directed to analyzer 90. Analyzer 90 may be configured to alter the attenuation ratio between the test beam and the reference beam. For example, as shown in FIG. 8, the analyzer may adjust the polarization of the reference beam to polarization 92, which is orthogonal to polarization 94 of the test beam or full numerical aperture (NA) signal exiting the analyzer. Analyzer 90 may include any suitable analyzer known in the art.

The test beam and the reference beam exiting analyzer 90 are directed by objective lens 96 to image plane 98. Objective lens 96 may be configured as described herein and may include any suitable optical components) known in the art. As shown in FIG. 8, the reference beam and the test beam are recombined at the image plane thereby causing interference between the reference beam and the test beam. A detector (not shown) may be located at the image plane. The detector may be configured as described above. In particular, the detector is configured to generate output representative of the interference between the test beam and the reference beam. As described further above, the interference increases the contrast between the output corresponding to the defects and the output corresponding to non-defective portions of the specimen. Therefore, the optical subsystem shown in FIG. 8 is configured for interference contrast enhancement of the defect output with common path construction between the test and reference beam paths.

The optical subsystem shown in FIG. 8 may be further configured as described herein. For example, the reference beam may be oriented such that the phase of the reference beam is substantially parallel to the phase of a portion of the test beam reflected from the defects. In particular, retarder 88 may be configured to orient the reference beam to be in-phase with the test beam. In addition, a system that includes the optical subsystem of FIG. 8 may be further configured as described herein.

As described above, systems configured for interference contrast enhancement may be configured to perform axial DIC. Alternatively, a system configured for interference contrast enhancement may be configured to perform lateral DIC. In one such embodiment, the self-generated reference beam may be a replicated copy of the signal (i.e., the reference beam may have substantially the same resolution as the test beam) reflected from neighboring or adjacent patterns on the specimen. The neighboring or adjacent patterns include structures that are by design identical to those illuminated by the test beam for cell-to-cell type comparisons. The cells may include array cells that include a repeating pattern of features. In this manner, in some embodiments, the reference beam and the test beam have substantially the same resolution but portions of the reference and test beams that interfere with each other are reflected from neighboring, substantially identical structures on the specimen. The neighboring structures may be identical by design, but the process(es) used to fabricate the structures on the specimen may render the neighboring structures not exactly identical. However, the neighboring structures formed on the specimen may be substantially identical.

Figure 9:
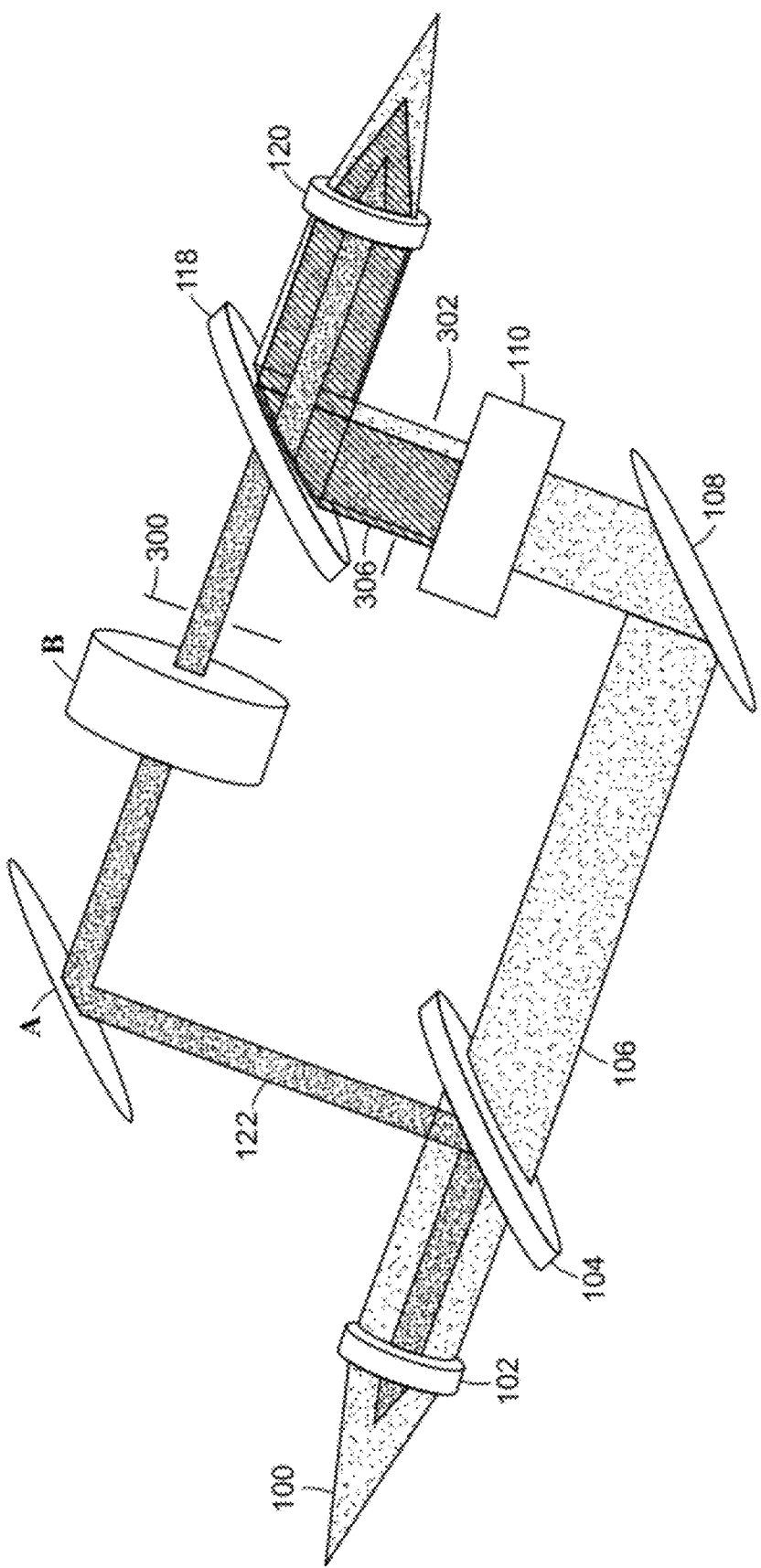

In one such embodiment, the optical subsystem is configured to laterally shift the reference beam with respect to the test beam. In these embodiments, the reference and test beams may be reflected from the same measurement spot on the specimen, and the reference beam may be laterally shifted from the test beam after the test and reference beams have been reflected from the specimen and the reference beam has been self-generated from the test beam. In another embodiment, the optical subsystem is configured such that the portions of the reference beam and the test beam that interfere with each other are reflected from substantially identical patterns spaced apart from each other on the specimen. In this manner, the reference beam may be shifted such that output from structures in the reference beam will overlap at the image plane with output from corresponding structures in the test beam. Therefore, the systems described herein may be configured to perform DIC or Nomarski type imaging. The lateral shift between the test beam and the reference beam may be less than one micron or on the order of nanometers. One embodiment of an optical subsystem that may be included in a system configured to generate output corresponding to defects on a specimen and that may use such a reference beam is illustrated in FIG. 9. Therefore, the optical subsystem shown in FIG. 9 may be included in a system configured for interference contrast enhancement by performing lateral DIC, in which the reference beam is a replicated copy of the test beam.

As shown in FIG. 9, light 100 reflected from a specimen (not shown) is collected by lens 102. Lens 102 may be configured as described above. For example, lens 102 may be an objective lens. The test beam portion of the reflected light is directed from the objective lens through beam splitter 104. Test beam 106 that passes through beam splitter 104 is directed by folding mirror 108 to optical component 110 located at the pupil of the optical subsystem. In some embodiments, if a second reference beam is not generated as described further herein, beam splitter 104 and folding mirror 108 may be eliminated from the optical subsystem. Beam splitter 104 and folding mirror 108 may be further configured as described herein and may include any suitable optical components known in the art.

Optical component 110 is configured to generate a laterally shifted reference beam 306 from test beam 106. In this manner, the laterally shifted reference beam is self-generated from the test beam. In addition, unlike the low resolution copy reference beams described herein, this laterally shifted reference beam will have about the same resolution as the test beam. The laterally shifted reference beam may also have about the same intensity as the test beam. In one embodiment, optical component 110 includes a wedge element. In some embodiments, the wedge element is formed of a birefringent material. In this manner, the test beam and the reference beam generated by optical component 110 may have orthogonal polarizations. In one embodiment, therefore, the reference beam and the test beam have polarizations that are orthogonal to each other. The wedge element includes a concave element and a convex element.

Figures 10, 11:
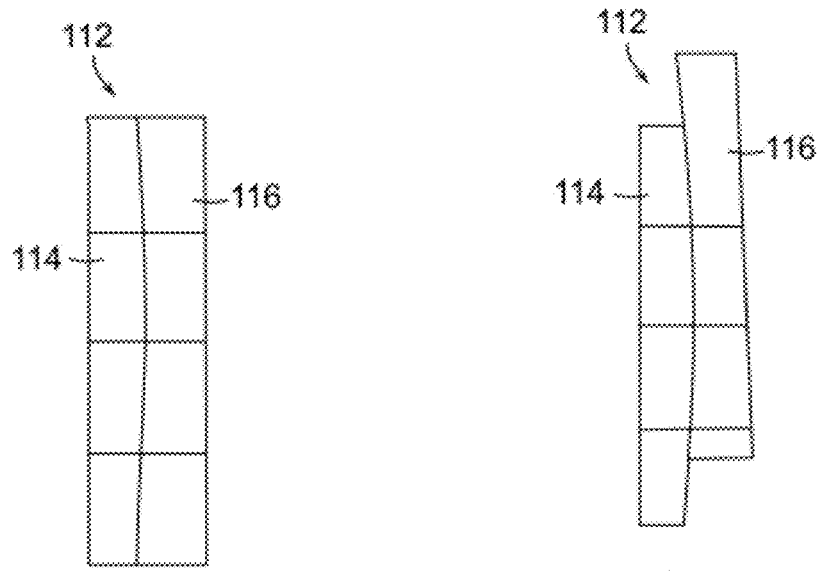
FIGS. 10-11 are schematic diagrams of a side view of one embodiment of a wedge element that includes a concave element and a convex element, which have different positions with respect to each other.

One embodiment of such a wedge element is illustrated in FIG. 10. As shown in FIG. 10, wedge element 112 includes convex element 114 and concave element 116. Convex element 114 and concave element 116 may include any suitable optical components known in the art. In one such embodiment, the system is configured to move one or more of the concave and convex elements with respect to each other to create lateral shift between the test beam and the reference beam. For instance, the system may include one or more mechanical components that are coupled to one or both of elements 114 and 116. The system may also include one or more additional components coupled to the mechanical component(s) that are configured to control the mechanical components). In this manner, the system may move one or both of the concave and convex elements with respect to one another.

The separation in the field between the reference beam and the test beam depends on the overall wedge angle of the wedge element. In this manner, by moving the concave element relative to the convex element or vice versa to change the overall wedge angle of wedge element 112, the system can control the lateral separation in the field between the reference and test beams. Preferably, the lateral separation in the field is such that output from corresponding structures in the test beam and the reference beam overlap in the image plane. In this manner, the lateral separation in the field may be varied depending on the arrangement of the patterned structures on the specimen.

As further shown in FIG. 9, after lateral separation of the reference and test beams, the laterally separated beams are directed by beam splitter 118 to objective lens 120. Beam splitter 118 and objective lens 120 may be further configured as described herein and may include any suitable optical components known in the art. Beam splitter 118 may be replaced with another suitable optical component such as a folding mirror or may not be included in the optical subsystem if a second reference beam is not generated by the optical subsystem as further described herein. The laterally separated beams are focused by the objective lens to an image plane of a detector (not shown). The detector may be configured as described herein. For example, the detector is configured to generate output representative of the interference between the test beam and the laterally shifted reference beam.

The interference between the test beam and the laterally shifted reference beam preferably increases contrast between the output corresponding to defects on the specimen and output corresponding to non-defective portions of the specimen. In particular, the laterally shifted, self-generated reference beam may be used for interference contrast enhancement of the defect output by minimizing the output from the structures on the specimen. In other words, the output from the structures in the laterally shifted, self-generated reference beam preferably produce deconstructive interference with the non-defective portions of the test beam to cancel non-defect output such as that from patterned structures on the specimen.

In some embodiments, the optical subsystems described herein such as that illustrated in FIG. 9 may use a combination of a low resolution reference beam and a laterally shifted reference beam. In this manner, the optical subsystem may be included in a system configured for interference contrast enhancement using both axial DIC and lateral DIC. In this configuration, the laterally shifted reference beam can be used to minimize the output corresponding to the nominal specimen pattern (including output from the structures on the specimen and background) as described above, and the low resolution reference beam can be used to increase the defect signal. As described above, the laterally shifted reference beam will have about the same resolution and intensity as the test beam. However, the intensity of the low resolution reference beam may vary depending on, for example, the DC portion of the test signal in order to maximize the defect signal and minimize the DC of the test signal. Therefore, the intensity of the low resolution reference beam may be higher than that of the replicated copy reference beam.

In particular, as shown in FIG. 9, light collected by lens 102 can be split by beam splitter 104 into reference beam 122 and test beam 106. Reference beam 122 is the low resolution reference beam that can be used to increase the defect signal. In addition, as described above, optical component 110 can be configured to generate a laterally shifted reference beam from test beam 106. Therefore, the laterally shifted reference beam can be used to minimize the nominal specimen pattern. In this manner, both the low resolution copy reference beam and the laterally shifted reference beam are self-generated from the test beam. In addition, both the low resolution copy reference beam and the laterally shifted reference beam are reflected from the same measurement spot on the specimen as the test beam.

As further shown in FIG. 9, reference beam 122 is directed by mirror A to optical component B. Mirror A and optical component B may be configured as described with respect to FIG. 5. In particular, the system may be configured to alter a position of the mirror to alter the relative phase between the reference and test beams. Alternatively, optical component B includes a group of two wedge prisms, and the system may be configured to move a first of the two wedge prisms with respect to a second of the two wedge prisms to alter the relative phase between the reference and test beams. In addition, as described above, the optical path length for reference beam 122 and test beam 106 may be substantially the same to avoid aberrations in the recombined beams due to differences in the optical paths.

In a different embodiment of the subsystem of FIG. 9, reference beam 122 may be used as the laterally shifted reference beam. This embodiment of the subsystem may, therefore, be included in a system configured for interference contrast enhancement using lateral DIC. In one such embodiment, test beam 106 may be shifted laterally with respect to reference beam 122 by folding mirror 108. The lateral shift of the test beam may be controlled by controlling a position of the folding mirror (e.g., by tilting the folding mirror). The position of the folding mirror may be altered and controlled as described further herein. In such an embodiment, the optical subsystem may not include optical components 110 and B. Alternatively, the test beam may be laterally shifted with respect to reference beam 122 using a wedge element such as that illustrated in FIGS. 10 and 11. In such an embodiment, the wedge element may be formed of an isotropic material. In some embodiments in which reference beam 122 is used as the laterally shitted reference beam, the reference beam can be generated from the test beam by splitting the test beam into two different beams that propagate along different optical paths and that have orthogonal polarizations. In one such embodiment, beam splitter 104 may be a polarization beam splitter. In additional embodiments, when reference beam 122 is used as the laterally shifted reference beam, the phase of reference beam 122 may also be controlled (or equalized) as described above to increase the defect output of the test beam.

In one embodiment of the optical subsystem shown in FIG. 9, therefore, interference contrast enhancement of the defect output may be obtained using a self-generated reference beam that is substantially the same as the test beam but laterally shifted for DIC or cell-to-cell comparisons and that propagates either along the same optical path (co-axially or collinearly) or is separated from the test beam along a portion of the optical path of the test beam.

Since the test and reference beams may travel across different optical paths after being split from each other and before being recombined, the test and reference beams may be imaged with different pupil apertures 300 and 302. For instance, in one embodiment, the optical subsystem is configured such that the test and reference beams are imaged with different pupil apertures. The different pupil apertures may include any suitable pupil apertures known in the art. In one embodiment, the test beam can be imaged in BF mode, and the reference beam can be imaged in DF mode using a pupil aperture different than that used for the test beam. In a different embodiment, the test beam can be imaged in DF mode, and the reference beam can be imaged in BF mode using a pupil aperture different than that used for the test beam. The optical subsystem shown in FIG. 9 and a system that includes the optical subsystem shown in FIG. 9 may be further configured as described herein.

As described above, a system configured for interference contrast enhancement may be configured for axial DIC or lateral DIC. However, as described above with respect to FIG. 9, a system configured for interference contrast enhancement may also be configured for axial and lateral DIC. In addition, various configurations described above may be combined into a system such that the system can be used to perform both axial and lateral DIC. In such embodiments, the system may be configured to use two reference beams to generate 3-beam interference. In one such embodiment, the optical subsystem is configured to create interference between the test beam and a reference beam and between the test beam and an additional reference beam. The reference beam has a lower resolution than the test beam, and the additional reference beam and the test beam are laterally shifted from each other. In this manner, the reference beam may be used for axial DIC while die additional reference beam may be used for lateral DIC. In addition, a system configured to perform both axial and lateral DIC may be configured such that only axial DIC may be performed for a specimen, only lateral DIC may be performed for the specimen, or both axial and lateral DIC may be performed for the specimen. For example, the optical subsystem shown in FIG. 9 may include one or more optical components (not shown) such as a shutter that can be controlled (e.g., by the system) to block one of the reference beams depending on the specimen being inspected. In another example, the system may be configured to control one or more of the components of the optical subsystems described herein to control which type of DIC is used for inspection of a specimen (e.g., the system may be configured to control the position of mirror A of the subsystem shown in FIG. 9 such that reference beam 122 is directed out of the optical path of the subsystem if, for instance, only lateral DIC is to be performed for a specimen). Such a system may be further configured as described herein.

Figure 13:
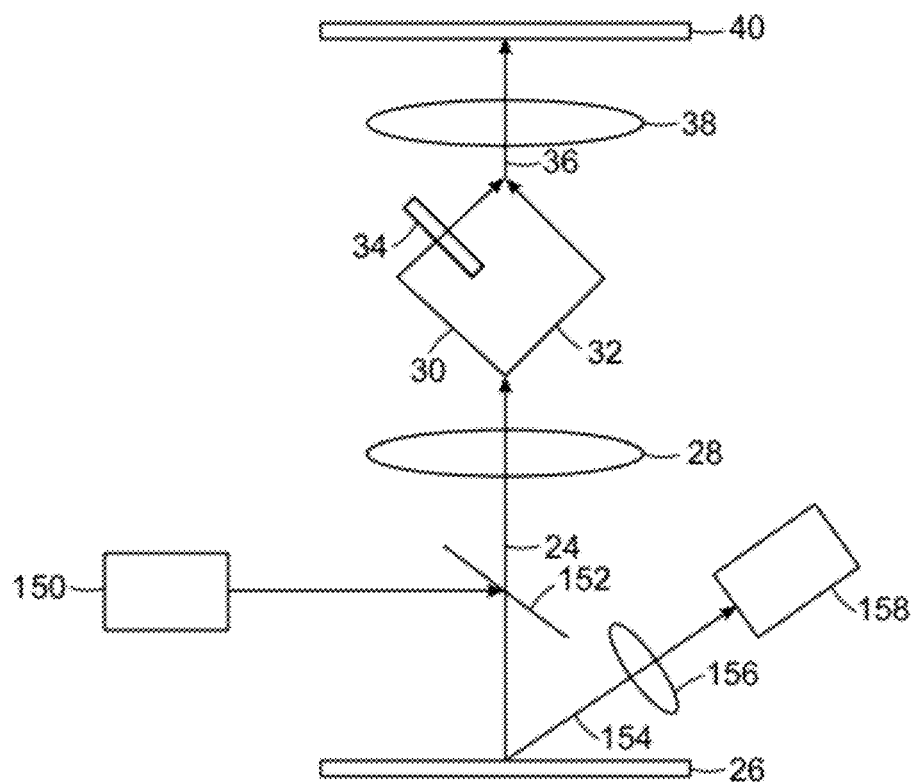
FIGS. 12-13 are partial schematic diagrams of a side view of various embodiments of a system configured to generate output corresponding to defects on a specimen.
Figure 12:
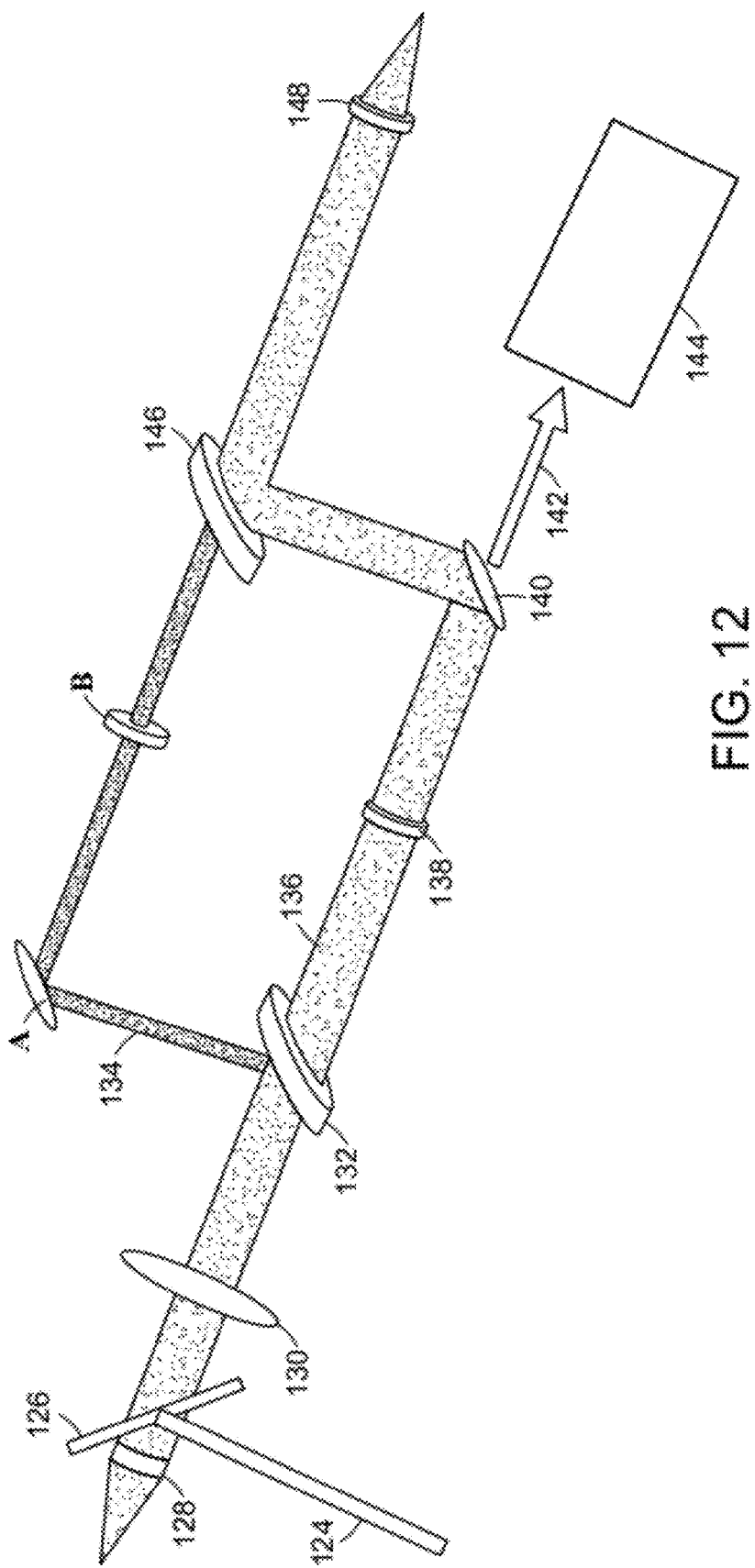

As described above, a system configured for interference contrast enhancement may be configured to perform axial and/or lateral DIC. Any of such systems may also be configured to perform inspection and/or review using an additional optical mode. In some embodiments, therefore, the systems described herein may be configured to perform defect detection and/or review with multiple optical modes. One embodiment of an optical subsystem that can be included in a system that can be used in interference contrast enhancement and BF modes for defect detection and/or review is illustrated in FIG. 12. In another embodiment, an optical subsystem that can be included in a system that can be used in interference contrast enhancement and DF modes for defect detection and/or review is illustrated in FIG. 13. In addition, each of these embodiments may be configured to perform multiple optical modes for defect inspection and/or review simultaneously (e.g., interference contrast enhancement simultaneously with BF or DF) or sequentially. Furthermore, the optical subsystems described herein may be configured for defect inspection and/or review using versatile and selectable mechanisms such as BF, DF, or interference contrast with minimal configuration change. In one such example, the DF detector shown in FIG. 13 and described further below may be added to the optical subsystem of FIG. 12 without substantial changes to the optical subsystem. In this manner, the optical subsystem can be included in a system that can perform defect inspection and/or review in BF mode, DF mode, interference contrast mode, or some combination thereof.

As shown in FIG. 12, illumination 124 generated by a light source (not shown) is directed to optical component 126, which may be a 50/50 beam splitter. Illumination 124 reflected by optical component 126 is focused by objective lens 128 to a specimen (not shown). Light reflected from the specimen passes through objective lens 128, optical component 126, and lens 130 to optical component 132. Objective lens 128 and lens 130 may be configured as described herein and may include any suitable optical components known in the art. Optical component 132 is a beam splitter in this embodiment. In particular, optical component 132 is configured to split the light reflected from the specimen into reference beam 134 and test beam 136. In this manner, reference beam 134 and test beam 136 may be reflected from the same measurement spot on the specimen. In addition, reference beam 134 is self-generated from test beam 136 and may be a low resolution copy reference beam that can be configured as described above. As such, reference beam 134 may be used by a system that includes such an optical subsystem to perform interference contrast enhancement by axial DIC.

Test beam 136 generated by optical component 132 passes through optical component 138. Optical component 138 may be configured to generate a laterally shifted reference beam (not shown) from the test beam. For instance, optical component 138 may be a wedge element such as that shown in FIGS. 10 and 11. In this manner, the test beam and the laterally shifted reference beam may be reflected from the same measurement spot on the specimen. Alternatively, optical component 138 may not be configured to generate the laterally shifted reference beam. In addition, optical component 138 may not be configured to alter the phase of the test beam. Light from optical component 138 is directed to folding mirror 140.

In one embodiment, the optical subsystem is configured to generate an additional test beam reflected from the specimen. For example, folding mirror 140 includes an aperture (not shown) in this embodiment. In this manner, folding mirror 140 is configured to generate additional test beam 142 by allowing a portion of test beam 136 to be transmitted through the folding mirror. In one such embodiment, the system includes an additional detector that is configured to generate BF output representative of the additional test beam. For example, as shown in FIG. 12, additional test beam 142 is directed to detector 144, which is configured to generate BF output representative of the additional test beam. Detector 144 may include any appropriate detector known in the art. The portion of the test beam reflected by folding mirror 140 is directed to beam splitter 146, which may include any suitable optical component known in the art.

Reference beam 134 is directed to mirror A and optical component B, both of which may be configured as described above. After passing through optical component B, the reference beam is directed to beam splitter 146. Beam splitter 146 combines the reference beam and the portion of the test beam reflected by folding mirror 140 to create interference between the test beam and the reference beam. The resulting interference beam is directed to lens 148, which focuses the interference beam to an image plane of a detector (not shown). Lens 148 may be configured as described herein and may include any suitable optical components) known in the art. The detector may be configured as described above. In particular, the detector is configured to generate output representative of the interference between the test and reference beams. The interference preferably increases the contrast between the output corresponding to defects on the specimen and output corresponding to non-defective portions of the specimen. In an additional embodiment, the output representative of the interference between the test and reference beams and the BF output are generated simultaneously. The embodiment of the optical subsystem shown in FIG. 12 may be further configured as described herein, and a system that includes such an optical subsystem may be further configured as described herein.

As described above, the systems described herein may be configured to perform DF defect inspection. One embodiment of a system that is configured to generate output corresponding to defects on a specimen is shown in FIG. 13. This system has the same general configuration as the system shown in FIG. 2 except that the system of FIG. 13 is configured to perform defect inspection and/or review using more than one optical mode. Elements that are shown in FIGS. 2 and 13 and that may be similarly configured have been indicated with the same reference numerals. These elements will not be further described herein.

As shown in FIG. 13, the optical subsystem includes light source 150. Light source 150 may be configured as described herein. Light generated by light source 150 is directed to beam splitter 152. Beam splitter 152 is configured to direct the light to specimen 26 at a substantially normal angle of incidence. Light 24 reflected from specimen 26 passes through beam splitter 152 and is collected by lens 28. Light 24 may be used for interference contrast enhancement defect detection and/or review as described further herein. In one embodiment, the optical subsystem is configured to collect an additional test beam scattered from the specimen. For example, the optical subsystem shown in FIG. 13 is configured to collect additional test beam 154 scattered from specimen 26. In one such example, the optical subsystem may include lens 156 that is arranged to collect light scattered from the specimen. Lens 156 may include any suitable optical components) known in the art. In one such embodiment, the system includes an additional detector that is configured to generate DF output representative of the additional test beam. For example, the system shown in FIG. 13 includes additional detector 158 that is configured to generate DF output representative of the additional test beam. In an additional embodiment, the output representative of the interference between the test and reference beams and the DF output are generated simultaneously.

Although only one DF collector and one DF detector (i.e., one DF channel) are shown in FIG. 13, it is to be understood that the system shown in FIG. 13 may include multiple DF channels. The DF channels may be arranged at any and different angles with respect to the specimen. In addition, although the system shown in FIG. 13 is configured to use the same light source for multiple optical modes, it is to be understood that the system may include multiple light sources, each of which is used for a different optical mode.

As shown by comparison of FIGS. 2 and 13, modification of the system shown in FIG. 2 to include DF detection and/or review capability did not result in changes to the interference contrast enhancement portion of the optical subsystem. Other embodiments of the systems described herein may also be modified in a similar manner to include DF detection capability. The embodiment of the optical subsystem shown in FIG. 13 may be further configured as described herein, and a system that includes such an optical subsystem may be further configured as described herein.

The systems described herein provide several advantages over currently used systems for defect inspection and/or review. In particular, the systems described herein are configured for detection and/or review of relatively small defects with reduction of background, improvement in the overall dynamic range, enhancement of the defect output through interference, or some combination thereof. Therefore, the systems described herein are capable of the detection and/or review of substantially small defects for current and future generations of semiconductor fabrication processes and overcome the limitations of current inspection and/or review systems in terms of weak defect output strength or lack of optimization mechanisms. In addition, the optical subsystems described herein are compatible with current inspection and/or review hardware and can be added to the hardware as an additional inspection and/or review mode. As such, the systems described herein can be used to greatly improve the defect detection and/or review capability of currently available inspection and/or review systems with minimal additional cost. Furthermore, the systems may be configured to have continuous adjustability of the characteristics of the reference beam for optimization of DOI detection and/or review. The systems described herein may also be configured to perform defect inspection and/or review using more than one optical mode simultaneously. For example, the systems may be configured to perform some combination of interference contrast enhancement, BF, and DF defect detection and/or review simultaneously.

In summary, all of the embodiments described above of a system configured for interference contrast enhancement may be configured such that the relative amplitudes between the reference and test beams may be adjusted. In addition, all of the embodiments described above of a system configured for interference contrast enhancement may be configured such that the relative phases between the reference and test beams may be adjusted. As described further above, some of the embodiments of a system configured for interference contrast enhancement may be configured to translate the reference beam relative to the test beam. In addition, as described further above, some of the embodiments of a system configured for interference contrast enhancement may be configured to generate a low resolution copy of the test beam that is used as the reference beam. Furthermore, as described further above, some of the embodiments of a system configured for interference contrast enhancement may be configured to translate a reference beam relative to the test beam and to generate a low resolution copy of the test beam that is used as a reference beam.

A system configured for interference contrast enhancement may have a number of different configurations as described above. For example, the optical subsystem of the system may include a concave/convex birefringent lens group. Alternatively, the optical subsystem may include a concave/convex lens group formed of normal glass or a non-birefringent material. In another example, the optical subsystem may include two wedge prisms formed of normal glass or birefringent material. In an additional example, the optical subsystem may include a waveplate with adjustable phase retardance. In yet another example, the optical subsystem may include an aperture with polarization dependent transmission.

As described above, systems configured to perform inspection and/or review based on interference contrast using a self-generated reference beam may be configured for interference contrast enhancement. Alternatively, systems configured to perform inspection and/or review based on interference contrast using a self-generated reference beam may be configured to perform relative phase measurements. For example, the systems described further herein may be used for defect inspection and/or review based on relative complex field information of the specimen being inspected. In particular, the complex field information may be obtained from interference of a test beam with a self-generated reference beam. The self-generated reference beam may include any of those described herein such as a low resolution reference beam or a tilted reference beam. In addition, the systems described further herein may be used for phase detection in relatively high speed specimen inspection using spatial fringe techniques or a phase-shifting technique. The systems that are configured for phase defect defection and/or review preferably include a detector (e.g., a TDI detector or a CCD detector) such that the phase information about defects on the specimen may be obtained as described further herein. Furthermore, all of the systems configured to perform relative phase measurements described further herein may also be configured to perform inspection and/or defect review using an additional optical mode such as BF and/or DF. The systems described further herein that are configured to perform relative phase measurements may be configured to perform inspection and/or review using an additional optical mode such as BF and/or DF as described further above.

In some embodiments, a system configured for relative phase measurements may be configured to perform the relative phase measurements using spatial fringe techniques. For example, one embodiment of a system that is configured to generate phase information about defects on a specimen includes an optical subsystem configured to combine a test beam and a reference beam to create an interference beam. The test beam and the reference beam are reflected from the specimen. The reference beam has a lower resolution than the test beam and is laterally shifted from the test beam in the pupil space of the optical subsystem to create spatial fringes at an image plane of the optical subsystem. The system also includes a detector configured to generate output representative of the spatial fringes at the image plane. The output can be used to determine the phase information about the defects. The system described above may be further configured as described herein.

In this manner, a system configured as described above may be configured for spatial fringe imaging with a self-generated reference beam. In particular, spatial fringe imaging may be used for complex field extraction using the low resolution (DC) image as the interference reference. A high frequency interference pattern may be generated with a tilted plane wave. This interference pattern may be used as a "ruler," which will be perturbed by a specimen complex field. In this manner, the specimen complex field information can be obtained by determining the perturbation from the straight line of the ruler. The embodiments described herein may extract the complex field information from this interference pattern using any suitable technique known in the art. One example of a suitable technique is described in "Spatial carrier heterodyne techniques for precision interferometry and profilometry: An overview.", M. Takeda, Proc. SPIE Vol. 1121, pp. 73-88 (1989), which is incorporated by reference as if fully set forth herein.

The systems described herein are particularly advantageous over interference contrast enhancement techniques for detecting relatively low intensity defects and/or high aspect ratio defects since such defects may not exhibit large changes in amplitude compared to a reference, but may exhibit large changes in phase compared to the reference. Therefore, such systems can detect relatively low intensity defects and/or relatively high aspect ratio defects with higher sensitivity by using the complex field information (i.e., amplitude and phase information) acquired by such systems instead of just intensity or amplitude information. The complex field information can be used with any defect detection method(s) and/or algorithm(s) known in the art to detect any type(s) of defects on the specimen.

Also, the systems described herein are advantageous over other commercially available inspection tools such as the Fathom™ patterned-wafer defect inspection tool, which is commercially available from nLine Corporation, Austin, Tex., and which uses Direct-to-Digital™ Holography (DDH) technology performed with an external-generated reference beam. For instance, as described further herein, the self-generated reference beams used in the embodiments described herein eliminate drifting or relative movement (vibration) between the reference and test beams.

Figure 14:
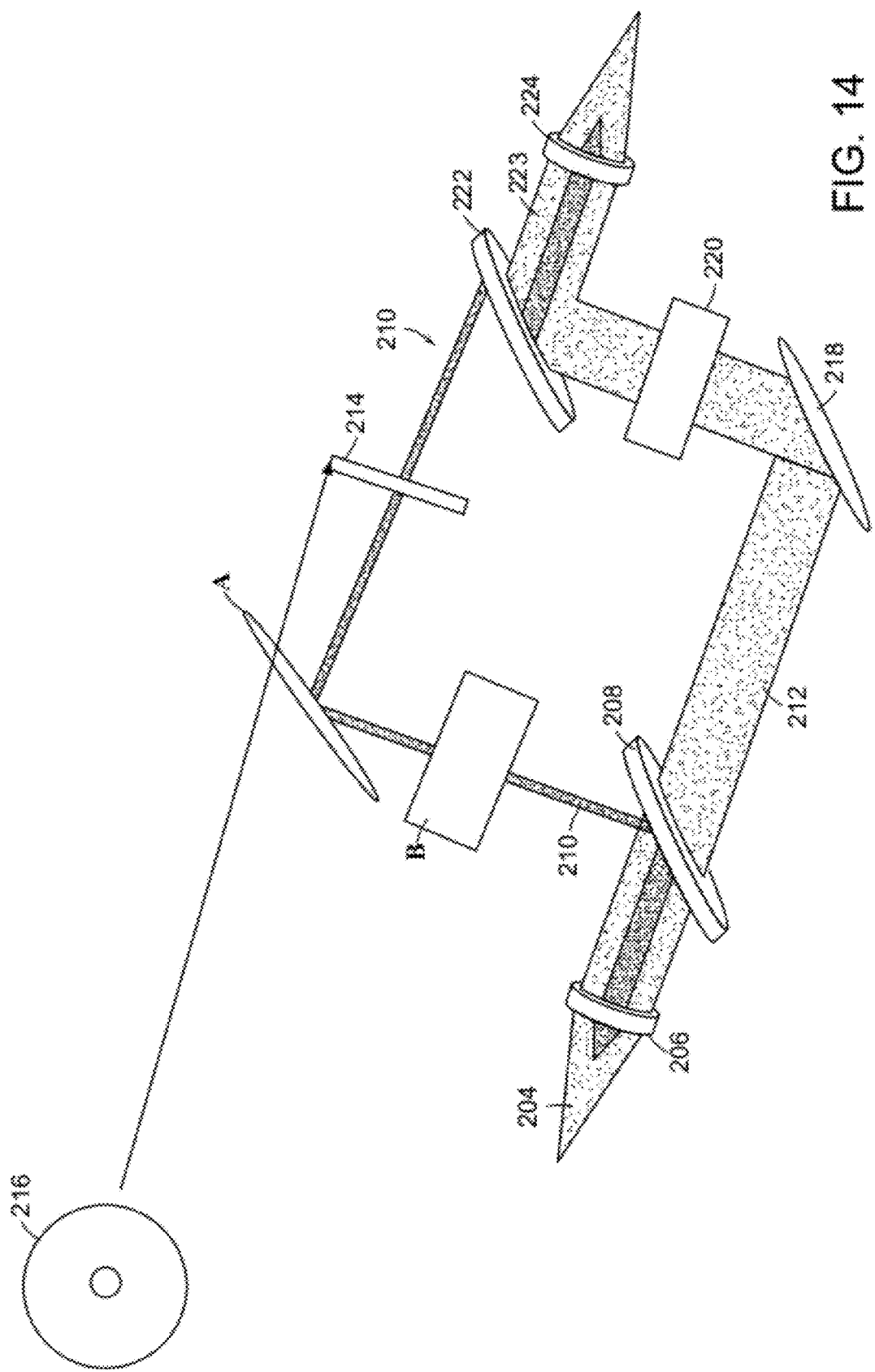
FIG. 14 is a partial schematic diagram of a side view of one embodiment of an optical subsystem that may be included in a system that is configured to generate phase information about defects on a specimen.

One embodiment of an optical subsystem that may be included in such a system embodiment is shown in FIG. 14. The optical subsystem is configured to combine a test beam and a reference beam to create an interference beam. As shown in FIG. 14, light 204 reflected from a specimen (not shown in FIG. 14) is collected by lens 206. Lens 206 may be configured as described above. For example, lens 206 may be an objective lens. Light collected by lens 206 is split by optical component 208 into reference beam 210 and test beam 212. In this manner, the reference beam is self-generated from the test beam reflected from the specimen. As such, the test beam and the reference beam are reflected from the specimen. In addition, the test beam and the reference beam are reflected from the same measurement spot on the specimen. The reference beam has a lower resolution than the test beam. Optical component 208 may include any suitable optical component known in the art such as a beam splitter.

In some embodiments, the optical subsystem includes optical component B and mirror A. Reference beam 210 is directed through optical component B to mirror A. Optical component B and mirror A may be configured as described above. For example, optical component B may include a group of two wedge prisms (not shown in FIG. 14), which may be configured as described above. As farther described above, the system may be configured to move a first of the two wedge prisms with respect to a second of the two wedge prisms to alter relative phase between the reference and test beams. In addition, mirror A may be a simple folding mirror. However, as described farther above, the system may be configured to alter a position of the mirror to alter relative phase between the reference and test beams. The system may include any suitable mechanical component(s) (not shown) that can be coupled to mirror A and that can be controlled (e.g., by a processor (not shown) such as that described above) to alter a position of the mirror.

As described above, reference beam 210 has a lower resolution than test beam 212. In this embodiment, the reference beam is also laterally shifted from the test beam in the pupil space of the optical subsystem to create spatial fringes at an image plane of the optical subsystem. For example, as shown in FIG. 14, reference beam 210 reflected by optical component 208 is directed to a module (not shown) that generates a low spatial frequency reference beam which is offset in the pupil of the optical subsystem. A resulting low spatial frequency reference beam 214 is also shown in cross-sectional view 216 in FIG. 14. The low spatial frequency reference module may be configured to offset the reference beam in the pupil of the optical subsystem to create high frequency interference fringes in the interference beam produced by combining the reference beam and the test beam. For instance, the low spatial frequency reference module may be configured to shift the reference beam in the pupil plane of the optical subsystem such that the reference beam comes in to the image plane of the optical subsystem as a tilted plane wave, which will produce spatial fringes in the combined interference beam. The optical elements in this module may be configured in such ways that the reduced optical length is substantially the same as the test beam. The low spatial frequency reference module may have any suitable configuration known in the art.

The optical subsystem shown in FIG. 14 may be configured such that the reference beam and the test beam have equivalent reduced optical paths. For example, test beam 212 is reflected by mirror 218, which directs the test beam to optical component 220. Optical component 220 may include a group of two wedge elements (not shown in FIG. 14) that is equivalent to that of optical component B. However, unlike mirror A and optical component B, mirror 218 and optical component 220 may not be configured to alter the phase of the test beam. For instance, the position of mirror 218 may be static or substantially constant. In addition, the positions of the wedge elements of optical component 220 may also be static or substantially constant. In this manner, aberrations in the recombined beam due to differences in the optical paths can be eliminated.

As shown in FIG. 14, the optical subsystem includes optical component 222, which is configured to recombine the reference beam and the test beam thereby creating interference beam 223. In one embodiment, optical component 222 is an appropriately positioned 45° beam splitter. The recombined beam or "interference beam" is directed through lens 224. Lens 224 may be configured as described above. Lens 224 is configured to direct the interference beam to an image plane (not shown in FIG. 14) of the optical subsystem. As described above, the reference beam has a lower resolution than the test beam and is laterally shifted from the test beam in the pupil space of the optical subsystem to create spatial fringes at the image plane. The system also includes a detector (not shown in FIG. 14) that is configured to generate output representative of the spatial fringes at the image plane. The output can be used to determine the phase information about the defects. For example, a processor (not shown in FIG. 14) such as that described above may be configured to use the output and any suitable method(s) and/or algorithm(s) to determine the phase information. The processor may also be configured to use the phase information and any suitable method(s) and/or algorithm(s) known in the art to detect any type(s) of defects on the specimen. The optical subsystem shown in FIG. 14 may be further configured as described herein. For example, the optical subsystem shown in FIG. 14 may be included in a system configured as an inspection and/or a review system. In addition, a system that includes an optical subsystem configured as shown in FIG. 14 may be further configured as described herein.

As described above, a system configured for relative phase measurements may be configured to perform the relative phase measurements using spatial fringe techniques. Alternatively, a system configured for relative phase measurements may be configured to perform the relative phase measurements using phase-shifting techniques and either a TDI detector or a CCD detector. In one embodiment, therefore, a system configured to generate phase information about defects on a specimen obtains the complex field information through interference measured using a phase-shifting technique and a TDI detector or a CCD detector. For example, the system includes an optical subsystem that is configured to combine a test beam and a reference beam to create an interference beam. The test beam and the reference beam are reflected from the specimen. The optical subsystem is also configured to alter the phase of the reference beam to create different interference beams. The optical subsystem may be further configured as shown and described herein.

The system also includes a detector that is configured to generate output representative of the different interference beams. In one embodiment, the detector includes a TDI detector. In other embodiments, the detector includes a CCD detector. The output can be used to determine the phase information about the defects. The optical subsystem is configured to scan the different interference beams over different segments of the detector. The different segments extend across a portion of one dimension of the detector. For example, the optical subsystem may be configured to apply different phase shifts to each one fourth of the integration stage of the detector. In addition, the optical subsystems shown and described further herein may be configured to scan the different interference beams over the different segments of the detector according to any of the embodiments described further herein.

Figure 15:
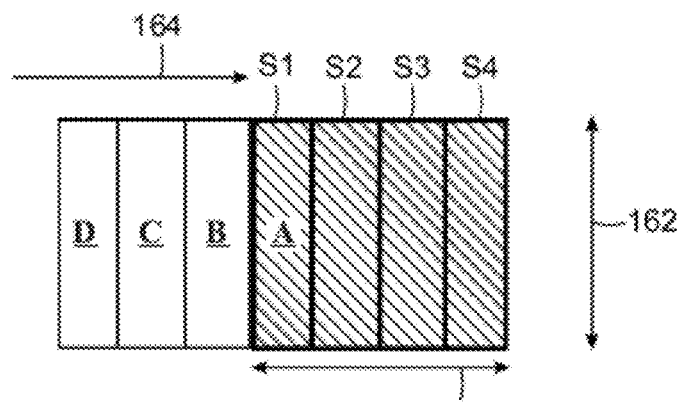
Figure 15:
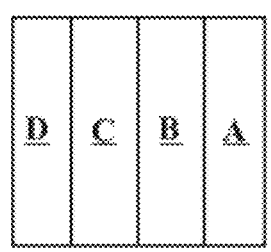
Figure 15:
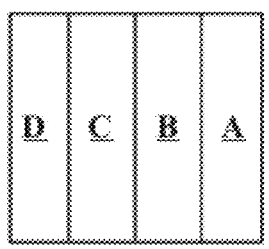
Figure 15:
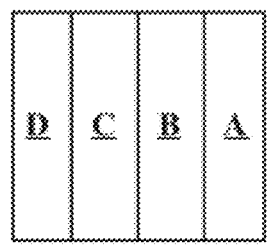

In one embodiment, the one dimension of the detector includes a width of the detector. One embodiment of a scanning technique that can be used to scan the different interference beams over different segments that extend across a portion of the width of the detector is illustrated in FIG. 15. As shown in FIG. 15, the detector includes four segments S1, S2, S3, and S4, each of which extend across only a portion of width 160 of the detector. For example, each of the segments may extend across only one fourth of the width of the integration stage of the detector. Each of segments S1, S2, S3, and S4 extends across entire height 162 of the detector. In addition, the specimen field may include four different columns corresponding to the segments of the detector.

During scanning of the detector with an interference beam generated by combining a test beam with a reference beam having a first phase (e.g., 0° phase), the optical subsystem scans the interference beam corresponding to only portion A of the specimen over segment S1 of the detector in the direction shown by arrow 164. After scanning this interference beam over segment S1, the illumination of the specimen by the optical subsystem may be reduced (e.g., by a shutter (not shown)), and the charge on the detector may be dumped. The optical subsystem then alters the phase of the reference beam (e.g., to 90° phase) to create a different interference beam. The optical subsystem may alter the phase of the reference beam as described herein. For this phase of the reference beam, the optical subsystem scans the interference beam corresponding to portions A and B of the specimen over segments S1 and S2 of the detector.

The optical subsystem may be configured to repeat this process for other different phases of the reference beam. For example, the phase of the reference beam may be altered to 180° phase, and an interference beam corresponding to portions A, B, and C of the specimen may be scanned over segments S1, S2, and S3 of the detector. In addition, the phase of the reference beam may be altered to 270° phase, and an interference beam corresponding to portions A, B, C, and D of the specimen may be scanned over segments S1, S2, S3, and S4 of the detector. In this manner, the system may be configured such that different phase shift is applied to different segments of the integration stage of the detector. In addition, the optical subsystem is configured to scan the different interference beams over the different segments of the defector sequentially.

In a different embodiment of the system configured to perform relative phase measurements using phase-shifting techniques described above, the optical subsystem is configured to alter the phase of the reference beam to create different interference beams for different swaths on the specimen. The different swaths may include only a portion of a field on the specimen. In one such embodiment, the one dimension of the detector includes a height of the detector.

Figure 16:
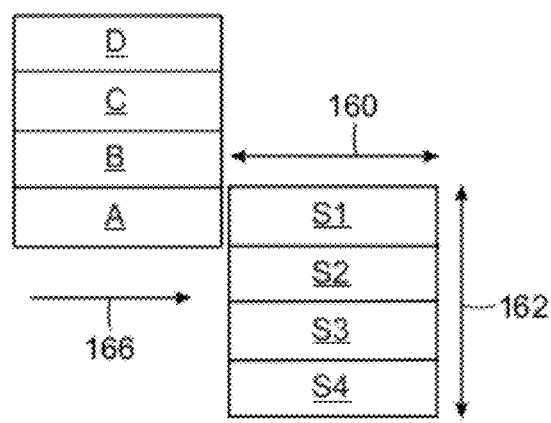

One embodiment of a scanning technique that can be used to scan the different interference beams over different segments that extend across a portion of the height of the detector is illustrated in FIG. 16. As shown in FIG. 16, the detector includes four segments S1, S2, S3, and S4, each of which extend across only a portion of height 162 of the detector. In this manner, each of the four segments may have a height that is about one fourth the height of the detector. Each of segments S1, S2, S3, and S4 extends across the entire width 160 of the detector. In addition, the specimen field may include four different swaths A, B, C, and D corresponding to the segments of the detector.

During scanning of the detector with an interference beam generated with a reference beam having a first phase (e.g., 0° phase), the optical subsystem scans the interference beam corresponding to only swath A of the specimen over segment S1 of the detector in the direction shown by arrow 166. After scanning the interference beam corresponding to swath A over segment S1 of the detector, the optical subsystem changes the phase of the reference beam (e.g., from 0° phase to 90° phase) to create a different interference beam for swaths A and B. The optical subsystem may change the phase of the reference beam as described further herein. The optical subsystem then scans this interference beam over segments S1 and S2. The optical subsystem may then change the phase of the reference beam (e.g., from 90° phase to 180° phase) to create another different interference beam for swaths A, B, and C. The optical subsystem scans this interference beam over segments S1, S2, and S3. The optical subsystem may again change the phase of the reference beam (e.g., from 180° phase to 270° phase) to create an additional different interference beam for swaths A, B, C, and D. The optical subsystem scans this interference beam over segments S1, S2, S3, and S4 of the detector.

In this manner, the optical subsystem is configured to scan the different interference beams over the different segments of the detector sequentially. In between each of the scans, the optical subsystem may reduce the illumination of the specimen, for example, by disposing a shutter (not shown) in an optical path of the light. In addition, the charge on the detector may be dumped between each of the scans.

In a different embodiment, the optical subsystem is configured to scan the different interference beams over the different segments of the detector substantially simultaneously. For instance, the optical subsystem may be configured to apply a fixed phase shift profile to the reference beam during data acquisition. The fixed phase shift profile may be substantially perpendicular to the scanning direction. The optical subsystem may be configured to combine such a reference beam with a test beam as described further herein to create an interference beam. In this manner, the interference beam for different swaths on the specimen will be different. Each of the different interference beams from the different swaths may be scanned over different segments of the detector. For example, each of the different interference beams may be scanned across a segment of the detector having one fourth the total height of the integration stage of the detector.

One embodiment of such scanning different interference beams across different segments of a detector is illustrated in FIG. 17. As shown in FIG. 17, the detector may include four segments S1, S2, S3, and S4, each of which extend across a portion (e.g., about one fourth) of height 162 of the detector. Each of the four segments extends across the entire width 160 of the detector. The interference beams that are scanned across the different segments of the detector are generated by combining a test beam with a reference beam having different phases. For example, the interference beam resulting from combining the test beam with a reference beam having a phase shift of 0° is scanned, across segment S1. The interference beam resulting from combining the test beam with a reference beam having a phase shift of 90° is scanned across segment S2. The interference beam resulting from combining the test beam with a reference beam having a phase shift of 180° is scanned across segment S3, and the interference beam resulting from combining the test beam with a reference beam having a phase shift of 270° is scanned across segment. S4.

One embodiment of an optical component, that may be included in the optical subsystems described herein to impart a different phase to different portions of a reference beam is illustrated in FIG. 18. In particular, according to one embodiment, the optical subsystem includes a staged phase wedge. Different stages of the staged phase wedge are configured to alter the phase of the reference beam to different degrees substantially simultaneously. For instance, as shown in FIG. 18, the staged phase wedge may include four stages 168, 170, 172, and 174, Each of the different stages may produce a phase shift, in the reference beam that is different by about 90°. FIG. 19 illustrates another embodiment of a staged phase wedge in which the phase changes across the wedge in a continuous manner unlike the step changes in phase across the wedge of FIG. 18. In particular, width 176 of the staged phase wedge of FIG. 19 may vary across the length of the wedge in a linear manner. The staged phase wedges shown in FIGS. 18 and 19 may be positioned in the optical subsystem at the same location as other phase-shifting components described herein. For example, a staged phase wedge may be used in place of optical component B shown in FIG. 5.

In a different embodiment, the optical subsystems described herein include an optical component that is configured to separate the reference beam into multiple reference beams. In one such embodiment, the optical subsystem is configured to alter the phase of the multiple reference beams such that each of the multiple reference beams has a different phase. The optical subsystem is also configured to combine the test beam and the multiple reference beams to create the different interference beams. The optical subsystem may be further configured to scan the different interference beams over the different segments of the detector substantially simultaneously, as shown in FIG. 17. In this manner, the optical subsystem may be configured to replicate the field into four equivalents, each of which may correspond to one fourth of the total swath height.

One embodiment of an optical component that may be used to separate the reference beam into multiple reference beams is shown in FIG. 20. In this embodiment, the optical component includes grating 178 that is configured to replicate the field at the pupil of the optical subsystem. As shown in FIG. 20, the grating is configured to separate reference beam 180 into multiple reference beams 182. Although the grating is shown to split the reference beam into four different reference beams, it is to be understood that the number of beams into which the reference beam is split may vary depending on, for example, the number of segments of the detector. This optical component may be disposed at the imaging pupil of any of the optical subsystems described herein.

Another embodiment of an optical component that may be used to separate the reference beam into multiple reference beams is shown in FIG. 21. In this embodiment, the optical component includes polarizing component 184 disposed between two birefringent plates 186 and 188. Therefore, this optical component may be configured to replicate the field with two birefringent plates. In particular, reference beam 190 is split into two reference beams 192 and 194 by birefringent plate 186. Polarizing component 184 is configured to alter the polarization of reference beams 192 and 194 such that the two reference beams can be split by birefringent plate 188 into four reference beams 196, 198, 200, and 202. The optical component shown in FIG. 21 may be located in the optical path of the reference beam at the field conjugate of the optical subsystem.

In yet another embodiment, the optical component that is used to separate the reference beam into multiple reference beams may include a combination of the optical components shown in FIGS. 20 and 21. For example, one of the birefringent plates of the optical component shown in FIG. 21 may be replaced with the grating shown in FIG. 20. In one such embodiment, the optical component also includes a polarizing component (e.g., polarizing component 184) disposed between the grating and the birefringent plate. Unlike the grating of FIG. 20, however, the grating that is used in this embodiment may be configured to split a reference beam into only two reference beams since the birefringent plate is used to split a reference beam into two reference beams for a total of four different reference beams.

Although the various embodiments described above for using a phase-shifting technique for scanning a detector involve scanning different interference beams over four segments of the detector, it is to be understood that the integration stage may be separated into more than four segments or fewer than four segments (e.g., two segments, three segments, etc.). In addition, the optical subsystem and/or the system may be configured to scan the different interference beams over the different segments of the detector according to the embodiments described above in any manner known in the art (e.g., via relative motion between the detector and the specimen or via an optical deflector).

The systems described above that are configured for relative phase measurements provide several advantages over currently used inspection and/or review systems. For example, the system embodiments described herein enable the detection and/or review of defects based on the relative phase information. Such inspection and/or review capability particularly benefits the detection of defects that only generate relatively small amplitude perturbations. These types of defects are particularly problematic for current and future generations of semiconductor fabrication. Therefore, the systems described herein may provide important defect detection and/or review capability for semiconductor fabrication. In addition, the reference beams used by the systems described herein are self-generated from the test beam reflected from the specimen being inspected or reviewed. Such a configuration, compared to a configuration utilizing an external reference, is not susceptible to system noise such as noise caused by vibration and/or focus errors, The systems described herein also allow phase detection utilizing a detector while the specimen is continuously scanned thereby resulting in lower overall cost and system complexity. Such capability is also better suited for relatively high speed specimen inspection than other interference-based inspection systems. Furthermore, the systems described herein can be configured so that they are compatible with current inspection and/or review hardware and can be added to existing systems to provide an additional inspection and/or review mode.

As noted above, the systems described herein are much less susceptible to system noise such as noise from vibration and are capable of relatively high speed specimen inspection. Therefore, the systems described herein are particularly suitable for integration into a process tool. In one embodiment, a system described herein may be coupled to a process tool. For example, the system may be disposed within the process tool. In some such embodiments, the system may be integrated into the process tool such that a specimen may be inspected by the system prior to, during, or after a step of the process performed by the process tool. In other embodiments, the system may be coupled to the process tool by a common handler, a common power source, a common processor, or a common environment. For example, the system may be configured as a separate module or tool that is coupled to the process tool by a common handler.

In yet other embodiments, the system may be configured as a "stand alone tool" or a tool that is not physically coupled to a process tool. However, such a system may be coupled to the process tool by a transmission medium, which may include wired and wireless portions.

The process tool may include any process tool known in the art such as a lithography tool, an etch tool, a deposition tool, a polishing tool, a plating tool, a cleaning tool, or an ion implantation tool. The process tool may be a "cluster tool" or a number of process modules coupled by a common handler.

The results of the inspection and/or review performed by the systems described herein may be used to alter a parameter of a process or a process tool using a feedback control technique, a feedforward control technique, or an in situ control technique. The parameter of the process or the process tool may be altered manually or automatically in any manner known in the art.

Further modifications and alternative embodiments of various aspects of the invention may be apparent to those skilled in the art in viewer of this description. For example, systems configured to generate output corresponding to defects on a specimen and systems configured to generate phase information about defects on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to generate phase information about defects on a specimen, comprising:
   an optical subsystem configured to combine a test beam and a reference beam to create an interference beam, wherein the test beam and the reference beam are reflected from the specimen, wherein the reference beam has a lower resolution than the test beam and is laterally shifted from the test beam in the pupil space of the optical subsystem to create spatial fringes at an image plane of the optical subsystem,
   wherein the optical subsystem comprises a wedge element comprising a concave element and a convex element, and wherein the system is further configured to move one or more of the concave and convex elements with respect to each other to create lateral shift between the test beam and the reference beam,
   wherein the optical subsystem further comprises a first pupil aperture and a second pupil aperture, wherein the first pupil aperture is different than the second pupil aperture, wherein the first pupil aperture is positioned in a path of the test beam reflected from the specimen and is not positioned in a path of the reference beam reflected from the specimen such that the first pupil aperture images the test beam and not the reference beam, and wherein the second pupil aperture is positioned in the path of the reference beam reflected from the specimen and is not positioned in the path of the test beam reflected from the specimen such that the second pupil aperture images the reference beam and not the test beam; and
   a detector configured to generate output representative of the spatial fringes at the image plane, wherein the output can be used to determine the phase information about the defects.

2. A system configured to generate phase information about defects on a specimen, comprising:
   an optical subsystem configured to combine a test beam and a reference beam to create an interference beam, wherein the test beam and the reference beam are reflected from the specimen, wherein the optical subsystem is further configured to alter phase of the reference beam to create different interference beams,
   wherein the optical subsystem comprises a wedge element comprising a concave element and a convex element, and wherein the system is further configured to move one or more of the concave and convex elements with respect to each other to create lateral shift between the test beam and the reference beam,
   wherein the optical subsystem further comprises a first pupil aperture and a second pupil aperture, wherein the first pupil aperture is different than the second pupil aperture, wherein the first pupil aperture is positioned in a path of the test beam reflected from the specimen and is not positioned in a path of the reference beam reflected from the specimen such that the first pupil aperture images the test beam and not the reference beam, and wherein the second pupil aperture is positioned in the path of the reference beam reflected from the specimen and is not positioned in the path of the test beam reflected from the specimen such that the second pupil aperture images the reference beam and not the test beam; and
   a detector configured to generate output representative of the different interference beams, wherein the output can be used to determine the phase information about the defects, wherein the optical subsystem is further configured to scan the different interference beams over different segments of the detector, and wherein the different segments extend across a portion of one dimension of the detector.

3. The system of claim 2, wherein the one dimension of the detector comprises a width of the detector.

4. The system of claim 2, wherein the optical subsystem is further configured to alter the phase of the reference beam to create the different interference beams for different swaths on the specimen, and wherein the one dimension of the detector comprises a height of the detector.

5. The system of claim 2, wherein the detector comprises a time delay integration detector.

6. The system of claim 2, wherein the optical subsystem is further configured to scan the different interference beams over the different segments of the detector sequentially.

7. The system of claim 2, wherein the optical subsystem is further configured to scan the different interference beams over the different segments of the detector substantially simultaneously.

8. The system of claim 7, wherein the optical subsystem further comprises a staged phase wedge, and wherein different stages of the staged phase wedge are configured to alter the phase of the reference beam to different degrees substantially simultaneously.

9. The system of claim 7, wherein the optical subsystem further comprises an optical component configured to separate the reference beam into multiple reference beams, wherein the optical subsystem is further configured to alter the phase of the multiple reference beams such that each of the multiple reference beams has a different phase, and wherein the optical subsystem is further configured to combine the test beam and the multiple reference beams to create the different interference beams.

10. The system of claim 9, wherein the optical component comprises a grating.

11. The system of claim 9, wherein the optical component comprises a polarizing component disposed between two birefringent plates.

12. The system of claim 9, wherein the optical component comprises a polarizing component disposed between a grating and a birefringent plate.

* * * * *